US010598677B2

(12) United States Patent
Nakajima et al.

(10) Patent No.: US 10,598,677 B2
(45) Date of Patent: *Mar. 24, 2020

(54) SMEAR TRANSPORTING APPARATUS, SMEAR IMAGE CAPTURE SYSTEM, AND SMEAR ANALYSIS SYSTEM

(71) Applicant: SYSMEX CORPORATION, Kobe-shi, Hyogo (JP)

(72) Inventors: Takayuki Nakajima, Kobe (JP); Katsuaki Yamaguchi, Kobe (JP); Tetsuya Oda, Kobe (JP); Seiya Shinabe, Kobe (JP); Mitsuo Yamasaki, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 111 days.

This patent is subject to a terminal disclaimer.

(21) Appl. No.: 15/662,732

(22) Filed: Jul. 28, 2017

(65) Prior Publication Data
US 2018/0031588 A1 Feb. 1, 2018

(30) Foreign Application Priority Data

Jul. 29, 2016 (JP) .................. 2016-150362
Jul. 21, 2017 (JP) .................. 2017-141632

(51) Int. Cl.
*G01N 35/00* (2006.01)
*G01N 1/31* (2006.01)
(Continued)

(52) U.S. Cl.
CPC ..... *G01N 35/00871* (2013.01); *G01N 1/2813* (2013.01); *G01N 1/312* (2013.01);
(Continued)

(58) Field of Classification Search
CPC .. G01N 1/2813; G01N 1/312; G01N 15/1468; G01N 15/1475; G01N 33/49;
(Continued)

(56) References Cited

U.S. PATENT DOCUMENTS

2001/0042817 A1* 11/2001 Harada ............. H01L 27/14837
250/208.1
2006/0024200 A1* 2/2006 Nishikiori ............ G01N 1/2813
422/67
(Continued)

FOREIGN PATENT DOCUMENTS

JP H03-57651 U 6/1991
JP 2000-74803 A 3/2000
(Continued)

*Primary Examiner* — Mekonen T Bekele
(74) *Attorney, Agent, or Firm* — Metrolex IP Law Group, PLLC

(57) ABSTRACT

A smear transporting apparatus transports a smear slide on which a sample is smeared to a smear-image capture apparatus. The smear transporting apparatus includes a smear-container transport part that transports a first smear container accommodating smear slides to a smear pickup position; a smear transfer part that picks a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and a storage that stores the first smear container and the second smear container.

12 Claims, 21 Drawing Sheets

(51) Int. Cl.
  *G01N 1/28* (2006.01)
  *G01N 15/14* (2006.01)
  *G01N 33/49* (2006.01)
  *G01N 35/02* (2006.01)
  *G06K 9/00* (2006.01)
  *G01N 35/04* (2006.01)

(52) U.S. Cl.
  CPC ..... *G01N 15/1468* (2013.01); *G01N 15/1475* (2013.01); *G01N 33/49* (2013.01); *G01N 35/026* (2013.01); *G06K 9/00134* (2013.01); *G01N 35/0099* (2013.01); *G01N 35/00732* (2013.01); *G01N 2015/1472* (2013.01); *G01N 2035/00138* (2013.01); *G01N 2035/00891* (2013.01); *G01N 2035/0413* (2013.01)

(58) Field of Classification Search
  CPC ........... G01N 35/00871; G01N 35/026; G01N 2015/1472; G01N 2035/00138; G01N 2035/00891; G01N 2035/0413; G01N 35/00732; G01N 35/0099; G06K 9/00134
  See application file for complete search history.

(56) References Cited

U.S. PATENT DOCUMENTS

| | | | |
|---|---|---|---|
| 2006/0263249 A1* | 11/2006 | Nakaya | G01N 1/2813 422/63 |
| 2007/0128073 A1 | 6/2007 | Tappen | |
| 2008/0193333 A1 | 8/2008 | Takahashi et al. | |
| 2008/0199066 A1* | 8/2008 | Watanabe | G06K 9/00127 382/133 |
| 2008/0201082 A1 | 8/2008 | Tohma et al. | |
| 2009/0155841 A1* | 6/2009 | Yamasaki | G01N 1/2813 435/40.51 |
| 2011/0170760 A1* | 7/2011 | Nordell | G06F 19/321 382/134 |
| 2011/0223632 A1* | 9/2011 | Yamada | G01N 1/312 435/40.51 |
| 2012/0003065 A1 | 1/2012 | Hirono et al. | |
| 2014/0093423 A1 | 4/2014 | Yamasaki et al. | |
| 2017/0343454 A1* | 11/2017 | Nakanishi | G01N 1/2813 |

FOREIGN PATENT DOCUMENTS

| | | |
|---|---|---|
| JP | 2006-47289 A | 2/2006 |
| JP | 2007-178251 A | 7/2007 |
| JP | 2009-518651 A | 5/2009 |
| JP | 2012-13954 A | 1/2012 |
| JP | 2014-70926 A | 4/2014 |
| JP | 2014-70932 A | 4/2014 |
| JP | 2014-70938 A | 4/2014 |
| JP | 2016-99324 A | 5/2016 |
| WO | 2007/067847 A2 | 6/2007 |
| WO | 2007/067847 A3 | 6/2007 |
| WO | 2016/084689 A1 | 6/2016 |

* cited by examiner

SMEAR TRANSPORTING APPARATUS, SMEAR IMAGE CAPTURE SYSTEM, AND SMEAR ANALYSIS SYSTEM

CROSS REFERENCE TO RELATED APPLICATIONS

This application claims priority from Japanese Patent Application No. 2016-150362, filed with the Japan Patent Office on Jul. 29, 2016, and from Japanese Patent Application No. 2017-141632, filed with the Japan Patent Office on Jul. 21, 2017, the entire contents of which are incorporated herein by reference.

BACKGROUND

The disclosure relates to a smear transporting apparatus, a smear image capture system, and a smear analysis system.

Heretofore, there has been known a microscope system in which: a smear slide being a microscope slide on which a biological sample (for example, blood) is smeared is transported to a microscope unit, and the microscope unit captures an image of the smear slide (see, for example, Japanese Patent Application Publication No. 2012-13954 (Patent Literature 1)).

As illustrated in FIG. 15, the microscope system described in Patent Literature 1 is configured such that smear slide 300 whose image is to be captured is taken out from multi-sheet cassette 301 accommodating smear slides 300, and after the microscope unit completes the image capturing, smear slide 300 whose image has been captured is returned to multi-sheet cassette 301. Carriage 303 attached to prop 302 movably in a vertical direction is provided with supply arm 304 and discharge arm 305. Supply arm 304 supplies stage 306 of the microscope unit with smear slide 300 in multi-sheet cassette 301. Discharge arm 305 discharges smear slide 300 from this stage 306.

A smear container such as the multi-sheet cassette described in Patent Literature 1 sometimes contains not only smear slides whose images are to be captured, but also smear slides whose images are not to be captured, for example, smear slides to be visually observed by the user. In a case where an image of a smear slide is automatically captured, an immersion oil is generally dropped on the smeared surface for the image capturing as described in, for example, Japanese Patent Application Publication No. 2014-70932. In a case where an image of a smear slide is captured using an immersion oil, the oil adheres to the smear slide. Hence, the smear slide returned to a multi-sheet cassette after the image capturing may cause the oil contamination of smear slides whose images are not to be captured and which are accommodated in the multi-sheet cassette. This may consequently decrease the handleability of smear slides in performing the visual observation.

In addition, heretofore, there has been known a smear transporting apparatus which transfers a smear slide prepared by a smear preparing apparatus to a smear image capture apparatus and accommodates the smear slide after its image has been captured (see, for example, Japanese Patent Application Publication No. 2014-70926 (Patent Literature 2)).

As illustrated in FIG. 24, the above-mentioned Patent Literature 2 describes smear transporting apparatus 403 which transports smear slide 400 from smear preparing apparatus 402 to smear image capture apparatus 401 and accommodates smear slide 400 whose image has been captured in rack 404. Smear image capture apparatus 401 of Patent Literature 2 puts immersion liquid in between an objective lens and smear slide 400 and increases numerical aperture of the objective lens to obtain a clear image. In this case, while smear slide 400 is transferred after an image of smear slide 400 is captured, the liquid attached to smear slide 400 may drop into smear transporting apparatus 403, which may result in contamination of an area where the liquid has dropped. Thus, smear transporting apparatus 403 is configured to include liquid receipt plate 403b under the transportation path of image-captured smear slide 400, to receive liquids dropped from transporting smear slide 400 with liquid receipt plate 403b, and to accommodate image-captured smear slide 400 in rack 404 above liquid receipt tray 403a.

The smear transporting apparatus illustrated in Patent Literature 2 requires to transfer and place an image-captured smear slide in a rack only in the area of a liquid receipt plate and a liquid receipt tray. It is desirable to enhance the flexibility of design of the smear transporting apparatus.

SUMMARY

One or more embodiments of smear transporting apparatus may transport a smear slide on which a sample is smeared to a smear-image capture apparatus. The smear transporting apparatus may include a smear-container transport part that transports a first smear container accommodating smear slides to a smear pickup position, the smear slides including a smear slide whose image is to be captured by the smear-image capture apparatus and a smear slide whose image is not to be captured by the smear-image capture apparatus; a smear transfer part that picks a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and a storage that stores the first smear container and the second smear container.

One or more embodiments of smear image capture system may includes: a smear-image capture apparatus that captures an image of a smear slide on which a sample is smeared; and a smear transporting apparatus that transports the smear slide to the smear-image capture apparatus. The smear transporting apparatus may include a smear-container transport part that transports a first smear container accommodating smear slides to a smear pickup position, the smear slides including a smear slide whose image is to be captured by the smear-image capture apparatus and a smear slide whose image is not to be captured by the smear-image capture apparatus; a smear transfer part that picks a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and a storage that stores the first smear container and the second smear container.

One or more embodiments of smear analysis system may include: a smear preparing apparatus that prepares a smear slide on which a sample is smeared; a smear-image capture apparatus that captures an image of the smear slide on which the sample is smeared; and a smear transporting apparatus that transports the smear slide supplied from the smear preparing apparatus to the smear-image capture apparatus.

The smear transporting apparatus may include a smear-container transport part that transports a first smear container accommodating smear slides to a smear pickup position, the smear slides including a smear slide whose image is to be captured by the smear-image capture apparatus and a smear slide whose image is not to be captured by the smear-image capture apparatus; a smear transfer part that picks a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and a storage that stores the first smear container and the second smear container.

One or more embodiments of smear transporting apparatus may include a holder configured to hold and transports a smear slide; a liquid receiver configured to receive liquid; and a driver configured to move the liquid receiver so as to receive liquid dropped from the smear slide.

One or more embodiments of smear image capture system may include a smear-image capture apparatus that captures an image of a smear slide on which a sample is smeared; and a smear transporting apparatus that transports the smear slide to the smear-image capture apparatus. The smear transporting apparatus may include a holder configured to hold and transport the smear slide whose image has been captured by the smear image capture apparatus; a liquid receiver configured to receive liquid; and a driver configured to move the liquid receiver so as to receive the liquid dropped from the smear slide.

Figure 1:
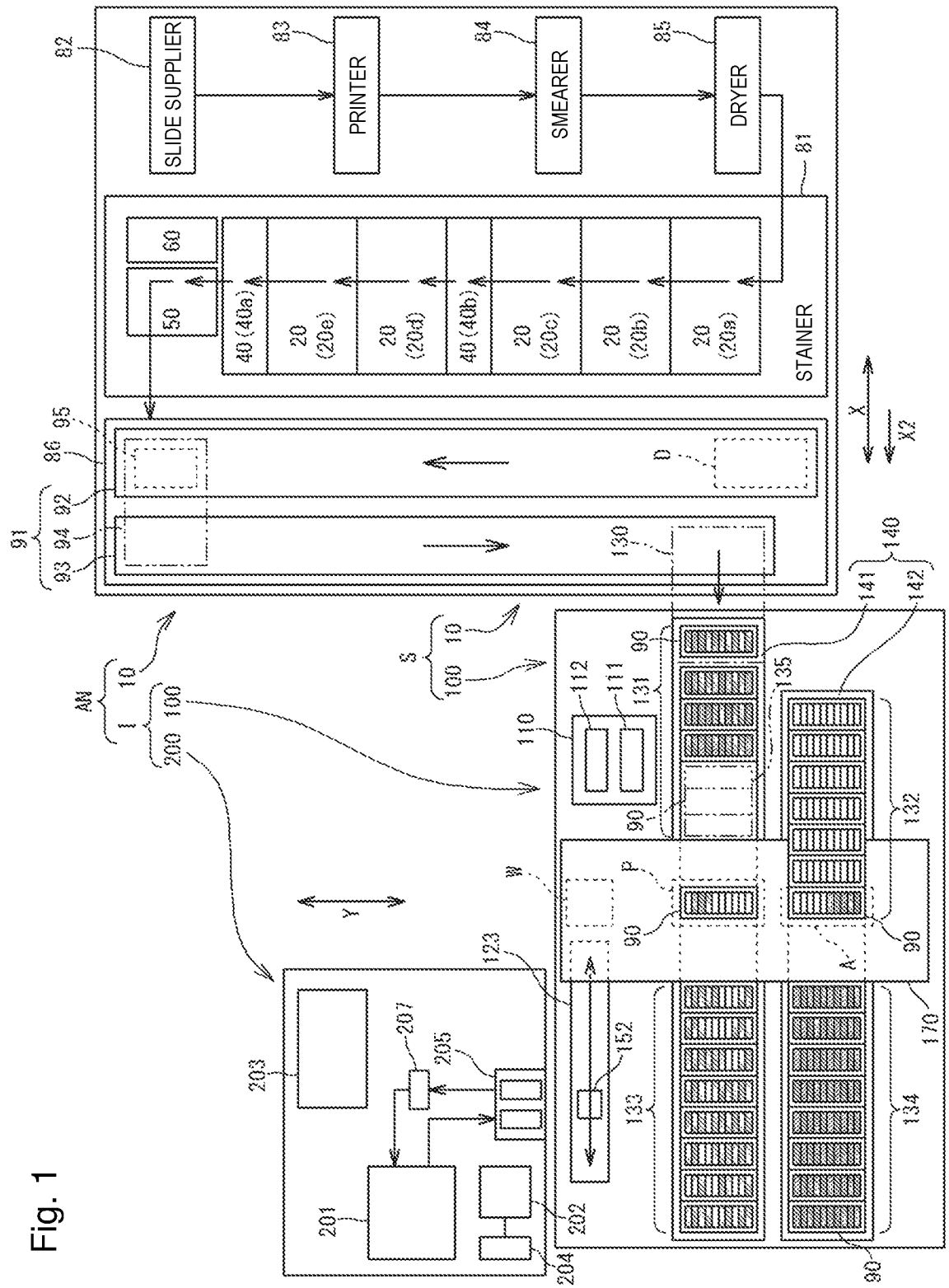
FIG. 1 is a plan explanatory diagram of one embodiment of a smear analysis system of one or more embodiments.

DETAILED DESCRIPTION (1) A smear transporting apparatus according one or more embodiments may be a smear transporting apparatus which transports a smear slide on which a sample is smeared to a smear-image capture apparatus. The smear transporting apparatus comprises: a smear-container transport part which transports a first smear container accommodating smear slides to a smear pickup position; a smear transfer part which takes out a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and a storage which stores the first smear container and the second smear container.

In the smear transporting apparatus according one or more embodiments, the smear slide whose image has been captured by the smear-image capture apparatus is accommodated in the smear container different from the smear container in which this smear slide has been accommodated before the image capturing. This makes it possible to suppress immersion oil contamination of smear slides whose images are not to be captured even when the image of the smear slide is captured using an immersion oil. Thus, when a smear slide whose image is not to be captured is visually observed, the user can visually observe a smear slide not contaminated with the oil by taking out the smear container accommodating the smear slide from the storage, thereby enhancing the smear slide handleability.

(2) In the smear transporting apparatus of (1), the smear transfer part may transfer the smear slide picked up from the first smear container to the smear-image capture apparatus, while a smear slide whose image is not to be captured by the smear-image capture apparatus remains accommodated in the first smear container transported to the smear pickup position. In this case, the smear slide whose image is not to be captured by the smear-image capture apparatus but which is to be visually observed under a microscope stays in the first smear container, thereby enabling efficient analysis.

(3) In the smear transporting apparatus of (1) or (2), the smear-container transport part may comprise: a first transport part which transports the first smear container accommodating the smear slides to the smear pickup position, and which transports the first smear container to the storage; and a second transport part which transports the second smear container accommodating the smear slide whose image has been captured by the smear-image capture apparatus to the storage. In this case, the transport part which transports the first smear container is different from the transport part for the second smear container accommodating the smear slide having a possibility of the immersion oil contamination. This makes it possible to suppress immersion oil contamination of smear slides whose images are not to be captured.

(4) The smear transporting apparatus of (3) may comprise: a first supply region where a first smear container accommodating smear slides is received from a smear preparing apparatus which prepares a smear slide; and a second supply region where a second smear container accommodating no smear slide is disposed. The first transport part may transport, to the storage, the first smear container which is supplied to the first supply region and transported to the smear pickup position. The second transport part may transport, to the storage, the second smear container which is supplied to the second supply region and accommodates the smear slide whose image has been captured by the smear-image capture apparatus. In this case, the transport path is divided into one for the first smear container and one for the second smear container, making it possible to use the two types of smear containers differently. In addition, the cleaning efficiency of the smear containers can be improved, for example, by frequently cleaning only the second smear container having a possibility of the immersion oil contamination.

(5) In the smear transporting apparatus of (4), the first supply region may comprise an interrupting-smear-container set region where a smear container accommodating a smear slide prepared manually is set. In this case, the analysis flexibility can be enhanced, for example, by giving priority to a smear slide that needs to be analyzed urgently.

(6) In the smear transporting apparatuses of (1) to (5), the smear transfer part may transfer the smear slide whose image is to be captured to the smear-image capture apparatus according to identification information acquired from the smear slide taken out by the smear transfer part. In this case, providing identification information to the smear slide enables the smear transfer part to transfer the smear slide whose image is to be captured to the smear-image capture apparatus.

(7) The smear transporting apparatus of (6) may comprise an identification-information acquisition part which acquires the identification information provided to the smear slide, the identification-information acquisition part comprising an image capture part which captures an image of a smear slide. A smear slide is transferred to the smear-image capture apparatus if the image of the smear slide captured by the image capture part includes identification information indicating that the image capturing by the smear-image capture apparatus is necessary. In this case, since the image captured by the image capture part includes the identification information, the smear slide can be transferred to the smear-image capture apparatus according to this image.

(8) In the smear transporting apparatuses of (1) to (7), the smear-image capture apparatus may comprise an oil applier which applies an oil to the sample smeared on the smear slide. In this case, the oil applied to the sample smeared on the smear slide by the oil application enhances the resolution of the captured image.

(9) A smear image capture system according one or more embodiments may be a smear image capture system comprising: a smear-image capture apparatus which captures an image of a smear slide on which a sample is smeared; and a smear transporting apparatus which transports the smear slide to the smear-image capture apparatus. The smear transporting apparatus comprises: a smear-container transport part which transports a first smear container accommodating smear slides to a smear pickup position; a smear transfer part which takes out a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and a storage which stores the first smear container and the second smear container.

In the smear image capture system of one or more embodiments, the smear slide whose image has been captured by the smear-image capture apparatus is accommodated in the smear container different from the smear container in which this smear slide has been accommodated before the image capturing. This makes it possible to suppress immersion oil contamination of smear slides whose images are not to be captured even when the image of the smear slide is captured using an immersion oil. Thus, when a smear slide whose image is not to be captured is visually observed, the user can visually observe a smear slide not contaminated with the oil by taking out the smear container accommodating the smear slide from the storage, thereby enhancing the smear slide handleability.

(10) In the smear image capture system of (9), the smear transfer part may transfer the smear slide picked up from the first smear container to the smear-image capture apparatus, while a smear slide whose image is not to be captured by the smear-image capture apparatus remains accommodated in the first smear container transported to the smear pickup position. In this case, the smear slide whose image is not to be captured by the smear-image capture apparatus but which is to be visually observed under a microscope stays in the first smear container, thereby enabling efficient analysis.

(11) A smear analysis system of one or more embodiments may be a smear analysis system comprising: a smear preparing apparatus which prepares a smear slide on which a sample is smeared; a smear-image capture apparatus which captures an image of the smear slide on which the sample is smeared; and a smear transporting apparatus which transports the smear slide supplied from the smear preparing apparatus to the smear-image capture apparatus. The smear transporting apparatus comprises: a smear-container transport part which transports a first smear container accommodating smear slides to a smear pickup position; a smear transfer part which takes out a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and a storage which stores the first smear container and the second smear container.

In the smear analysis system of one or more embodiments, the smear slide whose image has been captured by the smear-image capture apparatus is accommodated in the smear container different from the smear container in which this smear slide has been accommodated before the image capturing. This makes it possible to suppress immersion oil contamination of smear slides whose images are not to be captured even when the image of the smear slide is captured using an immersion oil. Thus, when a smear slide whose image is not to be captured is visually observed, the user can visually observe a smear slide not contaminated with the oil by taking out the smear container accommodating the smear slide from the storage, thereby enhancing the smear slide handleability.

(12) In the smear analysis system of (11), the smear transfer part may transfer the smear slide picked up from the first smear container to the smear-image capture apparatus, while a smear slide whose image is not to be captured by the smear-image capture apparatus remains accommodated in the first smear container transported to the smear pickup position. In this case, the smear slide whose image is not to be captured by the smear-image capture apparatus but which is to be visually observed under a microscope stays in the first smear container, thereby enabling efficient analysis.

The smear transporting apparatus, the smear image capture system, and the smear analysis system according one or more embodiments make it possible to enhance the handleability of smear slides in performing the visual observation.

A smear transporting apparatus in one aspect of this invention includes a holder which holds and transports a smear slide, a liquid receiver which receives, collects or catches liquid, and a driver which moves the liquid receiver to receive, collect or catch liquids dropped from a smear slide in the holder.

In the smear transporting apparatus in the one aspect of the invention, as described above, since the liquid receiver is moved, the liquid receiver can receive, collect or catch liquid dropped from a smear slide regardless of transportation paths of the smear slide, which can enhance the flexibility of design of the smear transporting apparatus.

In the smear transporting apparatus in the one aspect of the invention, it may be preferable that the driver moves the liquid receiver horizontally as the holder moves horizontally. With this configuration, the liquid receiver with the minimum dimensions can receive liquid dropped from a smear slide even in a case where the transportation distance of a smear slide is long.

In the smear transporting apparatus in the one aspect of the invention, it may be preferable that the driver moves the liquid receiver horizontally as the holder moves vertically. This configuration, for example, can avoid a smear slide held by the holder from contacting the liquid receiver when the holder moves downward. This configuration can also quickly move the liquid receiver to under a smear slide held by the holder when the holder moves upward.

It may be preferable that the smear transporting apparatus in the one aspect also includes an interlocking mechanism, which moves the liquid receiver horizontally as the holder moves vertically. This configuration does not require a control process to link movements of the holder and the liquid receiver and can interconnect the movements of the holder and the liquid receiver easily and promptly.

It may be preferable that the interlocking mechanism includes a belt which connects both the liquid receiver and the holder. This configuration connects the liquid receiver and the holder to the same belt; therefore, it can easily interconnect vertical movement of the holder and horizontal movement of the liquid receiver.

In the configuration in which the interlocking mechanism includes the belt, it may be preferable that the belt includes horizontal part extending horizontally and a vertical part extending vertically; the horizontal part connects to the liquid receiver, and the vertical part connects to the holder. This easily enables the liquid receiver to move horizontally and the holder to move vertically as the belt is driven.

It may be preferable that the interlocking mechanism moves the liquid receiver from the descending area of the holder and moves the liquid receiver under the holder as the holder moves upward. It can effectively prevent the liquid receiver laid under a smear slide from contacting a smear slide when the holder moves vertically to move a smear slide.

In the smear transporting apparatus of the aspect, it may be preferable that the driver passes the holder holding a smear slide and the liquid receiver over one smear container containing another smear slide whose image is to be captured, and then moves the holder and the liquid receiver to above another smear container. Since this configuration enables the liquid receiver to receive liquid dropped from the smear slide when the smear slide passes over the one smear container, it effectively prevents liquid from dropping on or into the one smear container containing the another smear slide whose image is to be captured.

A smear image capture system in another aspect of the invention includes a smear image capture apparatus which captures an image of a smear slide on which a sample is smeared and a smear transporting apparatus which transports the smear slide to the smear image capture apparatus. The smear transporting apparatus includes a holder which holds and transports the smear slide whose image has been captured by the smear image capture apparatus, a liquid receiver which receives, collects or catches liquid, and a driver which moves the liquid receiver to receive, collect or catch liquid dropped from a smear slide held by the holder.

In the smear image system in the another aspect of the invention, as described above, since the liquid receiver moves, the liquid receiver can receive, collect or catch liquid dropped from a smear slide regardless of transportation paths of the smear slide. Thus, this can provide a smear image capture system which is enable to enhance the flexibility of design of the smear transporting system.

In the smear image system in the another aspect, it may be preferable that the smear image capture apparatus is configured to capture an image of a smear slide with oil. This can increase numerical aperture of the objective lens at image capturing, which leads image capturing with high resolution.

In one or more embodiments, the flexibility of design of the smear transporting apparatus can be enhanced.

Hereinafter, embodiments of a smear transporting apparatus, a smear image capture system, and a smear analysis system are explained in detail with reference to the accompanying drawings. Note that the invention is not limited to these illustrative examples, and is intended to include meaning defined by the claims and equivalent to the claims as well as all modifications within the scope of the claims.

[Smear Analysis System]

As illustrated in FIG. 1, smear analysis system AN including a smear transporting apparatus according to one embodiment includes smear preparing apparatus 10, smear transporting apparatus 100, and smear-image capture apparatus 200. Smear preparing apparatus 10 prepared and supplies a smear slide to smear transporting apparatus 100. Smear transporting apparatus 100 supplies the smear slide to smear-image capture apparatus 200. Smear preparing apparatus 10, smear transporting apparatus 100, and smear-image capture apparatus 200 are capable of automatically performing a series of operations from preparation of smear slides with smeared samples such as blood to image capturing of the samples. Note that, in this Description, smear preparing apparatus 10 and smear transporting apparatus 100 constitute smear system S. In addition, a system or apparatus constituted by smear transporting apparatus 100 and smear-image capture apparatus 200 is referred to as smear image capture system I. Although this smear image capture system I is constituted by smear transporting apparatus 100 and smear-image capture apparatus 200, which are independent of each other in embodiments to be described later, it is also possible to constitute smear image capture system I as an apparatus integrated with smear transporting apparatus 100 and smear-image capture apparatus 200. For example, principal components of each apparatus can be stored in the same casing. Smear preparing apparatus 10 and smear image capture system I constitute the smear analysis system.

Note that this Description explains an X direction illustrated in FIG. 1 as a right-left direction, a Y direction as a front-rear direction, and a Z direction as a top-bottom direction. Moreover, a lower edge side in FIG. 1 indicates a front side, and an upper edge side therein indicates a rear side. Smear preparing apparatus 10 is disposed at a right side portion of smear transporting apparatus 100, and smear transporting apparatus 100 is disposed at a front side of smear-image capture apparatus 200. Smear transporting apparatus 100 is disposed in such a manner as to partially overlap with the front side of smear-image capture apparatus 200. Furthermore, in this Description, the word "traverse (ly)" may be used to mean the right-left direction, and the word "longitudinal" may be used to mean the front-rear direction.

[Smear Preparing Apparatus]

Figure 2A:
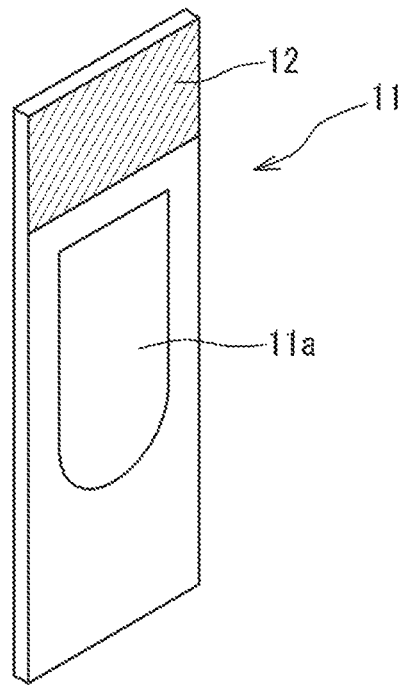
FIGS. 2A and 2B are explanatory perspective views of a smear slide.
Figure 2B:
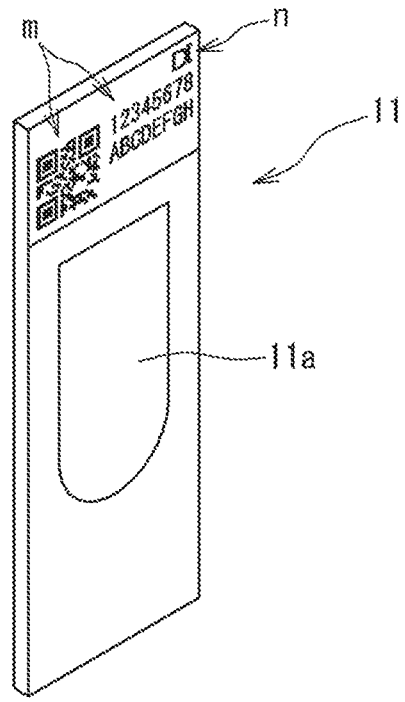

Smear preparing apparatus 10 according to this embodiment is an apparatus which prepares a smear slide 11 by performing processes such as smearing, drying, and staining on blood, which is a sample of a subject, on a microscope slide. As illustrated in FIGS. 2A and 2B, smear slide 11 is formed of a rectangular glass plate, and central section 11a thereof is smeared with a sample. An upper portion at one end portion in a longitudinal direction of smear slide 11 is provided with frost section 12 which is a region where identification information to be described later is typed (see FIG. 2A). Frost section 12 is a region coated with a synthetic resin or the like, so that a processing allowing the typing is performed. In this Description, smear slide 11 refers to not only microscope slides after the sample smearing process is completed in smear preparing apparatus 10, but also microscope slides provided with frost section 12 to be supplied to smear preparing apparatus 10 for the smearing process.

As illustrated in FIG. 2B, the identification information to be typed or printed on frost section 12 includes sample identification information m and image-capturing necessity identification information n. Sample identification information m is information for identifying a sample, such as sample number, date, reception number, and the name of a subject. Sample identification information m is typed on frost section 12 in such forms as a barcode, letters, and signs. Image-capturing necessity identification information n is information for identifying whether or not a sample is one whose image is to be captured by smear-image capture apparatus 200. Whether a sample is a sample whose image is to be captured by smear-image capture apparatus 200 or a sample to be visually tested under a microscope may have been inputted to a host computer in advance when a test is conducted. It is also possible to incorporate image-capturing necessity identification information n together with sample identification information m in, for example, one barcode. On the other hand, image-capturing necessity identification information n can also be typed on frost section 12 separately from sample identification information m. In the latter case, as image-capturing necessity identification information n, it is desirable to use letters, signs, or the like which are not used for sample identification information m. Examples of image-capturing necessity identification information n can include various letters, for example, alphabets such as A, B, and C, and various signs such as ▲, ●, ■, and ♦, but are not limited thereto. Even in the case where alphabets are used as sample identification information m, a sign obtained by overlaying or combining two alphabet letters with each other may be used as image-capturing necessity identification information n, for the distinction. Note that although sample identification information m is normally information for identifying a sample, it is also possible to inquire of an external host computer whether image capturing of the sample is necessary or not on the basis of this sample identification information m to thereby determine whether smear slide 11 is one whose image is to be captured or not on the basis of a result obtained from the host computer. Thus, this sample identification information m is also included in "identification information on whether image capturing by the smear-image capture apparatus is necessary or not".

Figure 3:
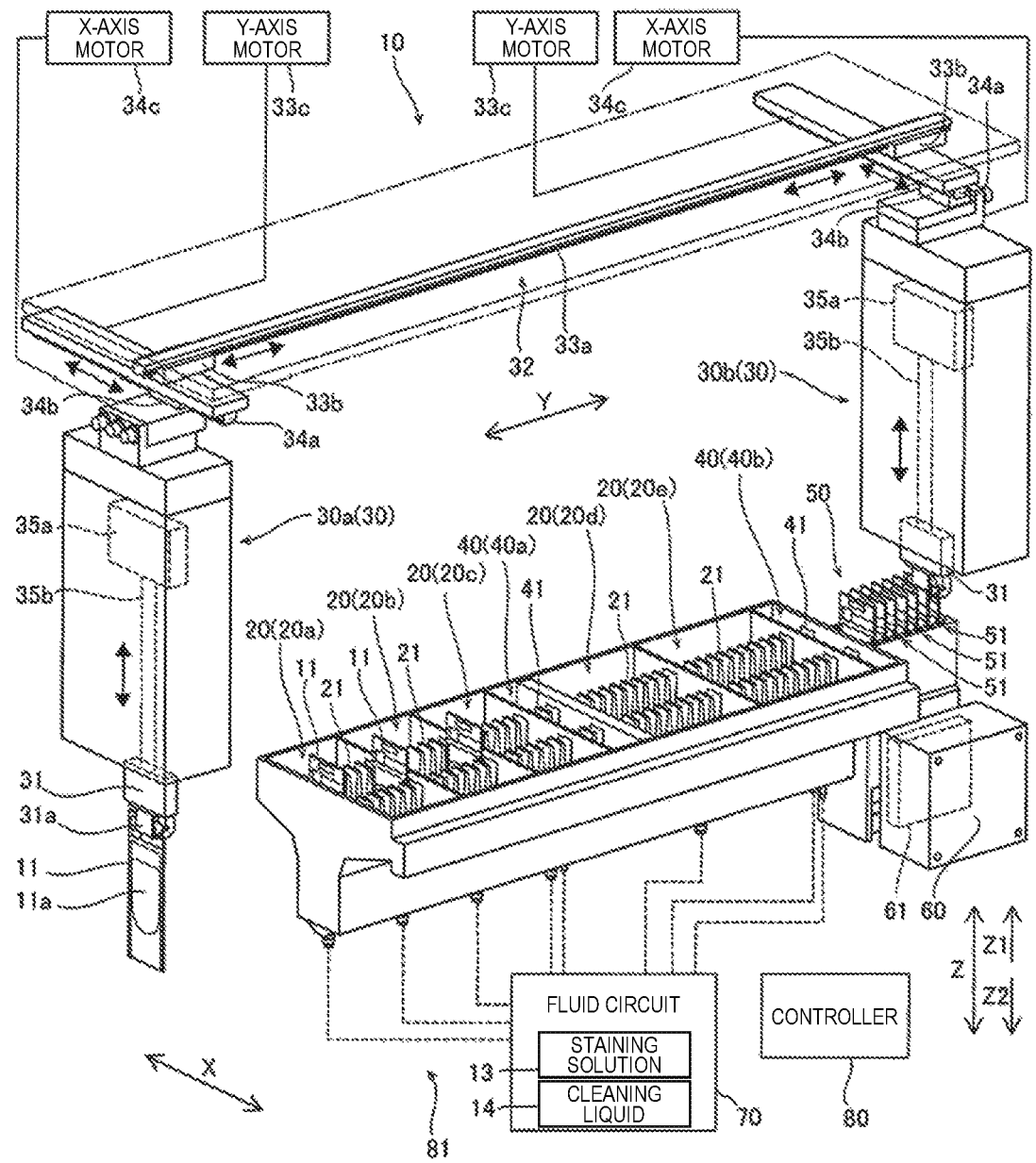
FIG. 3 is an explanatory perspective view of stain chambers and a transfer unit of a smear preparing apparatus.

As illustrated in FIG. 1 or 3, smear preparing apparatus 10 includes stain chambers 20, transfer unit 30, cleaning chambers 40, drying chamber 50, blower unit 60, slide supplier 82, printer 83, smearer 84, dryer 85, and slide storage 86. Stain chambers 20, cleaning chambers 40, drying chamber 50, and blower unit 60 constitute stainer 81 in smear preparing apparatus 10. In this embodiment, smearer 84, stainer 81, and dryer 85 prepare a smear slide 11 by smearing a sample on a slide. Smear preparing apparatus 10 further includes fluid circuit 70 for supplying and discharging staining solution 13 and cleaning liquid 14 to and from stain chambers 20 and cleaning chambers 40, respectively; and controller 80 for controlling the operations of transfer unit 30, blower unit 60, and so forth. Controller 80 is a computer including unillustrated CPU, memory, and so forth.

Slide supplier 82 stores numerous smear slides 11 yet to be used before a sample is smeared. Slide supplier 82 supplies printer 83 with smear slides 11 one by one before smearing. Printer 83 can type or print various information such as the sample identification information, the image-capturing necessity identification information, and so forth on frost section 12 which is the region of smear slide 11 where typing is performed. Printer 83 transfers typed smear slide 11 to smearer 84.

Smearer 84 aspirates a sample with an unillustrated sample aspiration mechanism, smears the sample on central section 11a of smear slide 11 transferred from printer 83. After the smearing process, smearer 84 transfers smear slide 11 to dryer 85.

Dryer 85 receives smear slide 11 with the smeared sample from smearer 84, and has a function of drying central section 11a with the smeared sample.

In stainer 81, smear slide 11 smeared with the sample dried by dryer 85 is stained in stain chambers 20a, 20b, 20c, 20d, 20e and cleaned in cleaning chambers 40a, 40b. Then, smear slide 11 is dried in drying chamber 50. When the staining of smear slide 11 is completed, stained smear slide 11 is transferred to slide storage 86. Transfer unit 30 transfers smear slide 11 between these components.

Stain chambers 20 are each formed in a shape of container in which a staining solution is stored so that smear slide 11 with the smeared sample can be immersed therein. Moreover, each of cleaning chambers 40 is also formed in a shape of container in which a cleaning liquid is stored so that stained smear slide 11 can be immersed therein. In smear preparing apparatus 10 according to this embodiment, three stain chambers 20a, 20b, 20c, cleaning chamber 40a, two stain chambers 20d, 20e, and cleaning chamber 40b are disposed in this order along the Y-axis direction. These chambers are integrally formed as a single chamber using a synthetic resin. Note that the numbers of stain chambers 20 and cleaning chambers 40 should be selected as appropriate in accordance with the content of the staining process, the number of steps, and so on. The numbers are not particularly limited.

In stain chambers 20 and cleaning chambers 40, partitions 21, 41 are provided respectively. Smear slide 11 is inserted between partitions 21 next to each other or between partitions 41 next to each other, and held or positioned by these partitions 21, 41.

Transfer unit 30 is provided to grip and transfer smear slide 11 with the smeared sample. Transfer unit 30 is capable of putting each smear slide 11 one by one in and out stain chambers 20 or cleaning chambers 40. As the configuration of transfer unit 30 for putting each smear slide 11 in and out one by one in this manner, various configurations can be adopted. In this embodiment, as illustrated in FIG. 3, a three-axis coordinate robot is adopted which is movable in horizontal directions (X direction and Y direction) and in the top-bottom direction (Z direction) or vertical direction, and includes hand members 31 for gripping smear slide 11. As hand member 31, it is possible to use, for example, an open-close mechanism capable of grasping smear slide 11 from both sides, or an aspiration mechanism which grasps smear slide 11 by suction on a predetermined spot thereof at a negative pressure.

Transfer unit 30 includes first transfer part 30*a* and second transfer part 30*b*. Both of first transfer part 30*a* and second transfer part 30*b* are disposed above (Z1 direction) stain chambers 20 and cleaning chambers 40. First transfer part 30*a* and second transfer part 30*b* are movable in the horizontal directions (X direction and Y direction) independently of each other by movement mechanism 32.

Movement mechanism 32 includes Y-axis rail 33*a* and Y-axis sliders 33*b* located in the Y direction, X-axis rails 34*a* and X-axis sliders 34*b* located in the X direction, Y-axis motors 33*c*, and X-axis motors 34*c*. As Y-axis motors 33*c* and X-axis motors 34*c*, for example, stepping motors and servomotors can be adopted.

Y-axis sliders 33*b* are attached to a bottom surface side (Z2 direction) of Y-axis rail 33*a*, and movable along Y-axis rail 33*a*. Y-axis motors 33*c* move Y-axis sliders 33*b* in the Y direction with an unillustrated transmission mechanism. As the transmission mechanism, for example, a belt-pulley mechanism, a rack-pinion mechanism, or the like can be used.

X-axis rails 34*a* are fixed to bottom surfaces of Y-axis sliders 33*b*. X-axis sliders 34*b* are attached to bottom surface sides (Z2 direction) of X-axis rails 34*a*, and are movable along X-axis rails 34*a*. X-axis motors 34*c* move X-axis sliders 34*b* in the X direction with an unillustrated transmission mechanism.

Y-axis sliders 33*b*, X-axis rails 34*a*, X-axis sliders 34*b*, X-axis motors 34*c*, and Y-axis motors 33*c* are respectively provided in pairs. To bottom surface sides of the pair of X-axis sliders 34*b*, first transfer part 30*a* and second transfer part 30*b* are attached, respectively. First transfer part 30*a* and second transfer part 30*b* are movable independently of each other in the X direction along separate X-axis rails 34*a*. Moreover, first transfer part 30*a* and second transfer part 30*b* are movable independently of each other in the Y direction along the same Y-axis rail 33*a*.

The configurations of first transfer part 30*a* and second transfer part 30*b* are the same. First transfer part 30*a* and second transfer part 30*b* each include Z-axis motor 35*a* and transmission mechanism 35*b* for elevating and lowering hand member 31. Z-axis motor 35*a* is capable of elevating and lowering hand member 31 with transmission mechanism 35*b*.

Hand member 31 includes a pair of gripping plates 31*a*. Hand member 31 is capable of gripping one smear slide 11 in a thickness direction from both sides with the pair of gripping plates 31*a*. The pair of gripping plates 31*a* grip smear slide 11 by respectively coming into contact with a front surface and a back surface of smear slide 11. Of the pair of gripping plates 31*a*, gripping plate 31*a* at the back surface side is capable of moving smear slide 11 in the thickness direction. Gripping plates 31*a* can be moved using an actuator, for example, an air cylinder, a motor, a solenoid, or the like.

Drying chamber 50 is disposed in such as manner as to be substantially aligned with stain chambers 20 and cleaning chambers 40 along the Y direction in which stain chambers 20 and cleaning chambers 40 are arranged. Drying chamber 50 is provided to dry smear slide 11 having been subjected to the staining process and the cleaning process. Drying chamber 50 is partitioned by partitions 51, and is capable of holding smear slide 11 between partitions 51 next to each other. Inside drying chamber 50, an air passage (unillustrated) is formed. This air passage is connected to blower unit 60.

Blower unit 60 is provided to supply hot air to smear slide 11 held in drying chamber 50. Heater 61 for heating air is provided between blower unit 60 and drying chamber 50.

Figure 4:
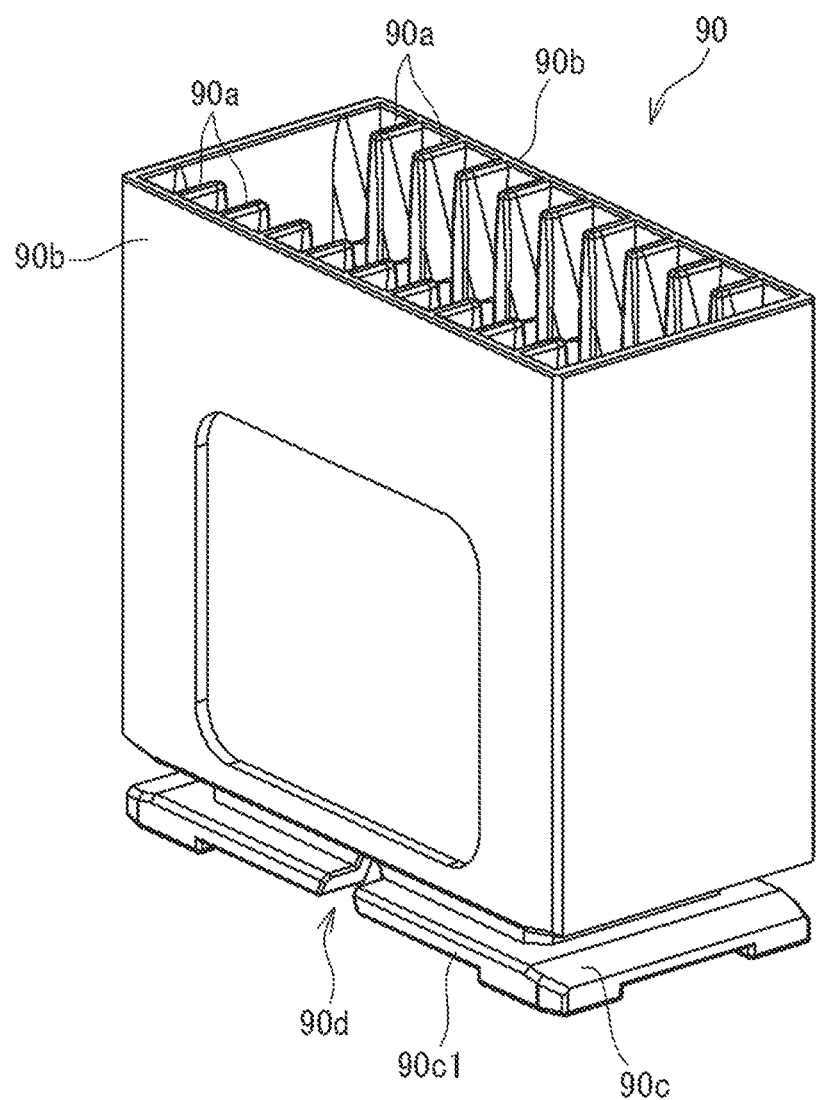
FIG. 4 is an explanatory perspective view of a smear container.

After the staining, cleaning, and drying processes are completed, transfer unit 30 transfers smear slide 11 to slide storage 86. Slide storage 86 includes Magazine transport part 91 which transports slide magazine 90 serving as a smear container. Slide magazine 90 is capable of holding stained smear slides 11. As illustrated in FIG. 4, slide magazine 90 has a box shape whose top surface is opened, and partitions 90*a* are provided inside slide magazine 90. Partitions 90*a* are formed on inner surfaces of longitudinal walls 90*b* opposite to each other. Partitions 90*a* formed on the inner surface of one of walls 90*b* are formed at positions opposite to partitions 90*a* formed on the inner surface of the other wall 90*b* at the opposite side. In this embodiment, slide magazine 90 can accommodate ten smear slides 11.

Figure 5:
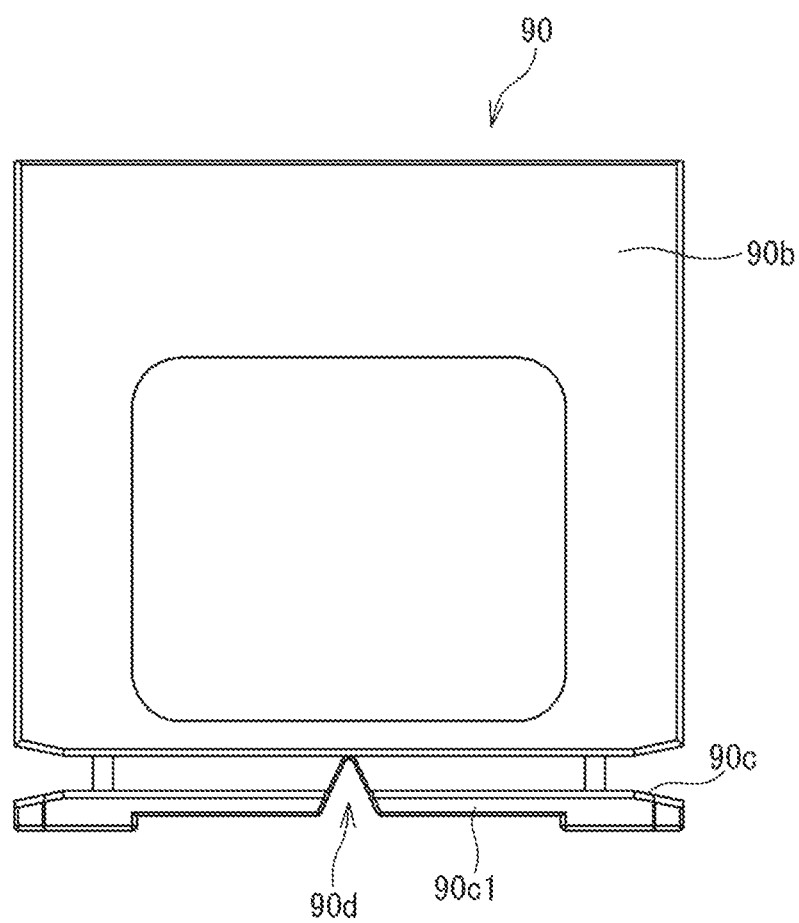
FIG. 5 is an explanatory front view of the smear container.

In base 90*c* of slide magazine 90, triangular notch 90*d* is formed which engages with guide rail 145 of smear transporting apparatus 100 to be described later. As illustrated in FIG. 5, this notch 90*d* is a triangular notch when slide magazine 90 is seen in a front view of wall 90*b* in a longitudinal direction of slide magazine 90. Notch 90*d* is formed across the entire length direction of a shorter side of base 90*c*.

Magazine transport part 91 includes magazine carry-in path 92 capable of storing empty slide magazines 90, magazine carry-out path 93 capable of storing slide magazines 90 storing smear slides 11, and traverse transfer mechanism 94 extending from magazine carry-in path 92 to magazine carry-out path 93. In Magazine transport part 91, when the user sets empty slide magazine 90 in introduction section D of magazine carry-in path 92, slide magazine 90 is automatically transported toward smear storage position 95.

After drying chamber 50 completes the drying process, transfer unit 30 grasps and raises smear slide 11, and stores smear slide 11 in an empty storage section of slide magazine 90 disposed at smear storage position 95. When the storage section is filled, traverse transfer mechanism 94 traversely transfers slide magazine 90 from magazine carry-in path 92 to magazine carry-out path 93. Slide magazine 90 traversely transferred to magazine carry-out path 93 is automatically transported frontward. When slide magazine 90 is transported to the frontmost side, traverse transfer unit 130 transfers slide magazine 90 to magazine buffer region 131, which is a first supply region of smear transporting apparatus 100.

[Smear Transporting Apparatus]

Smear transporting apparatus 100 includes: smear-container transport part 140 for transporting slide magazine 90, which is a smear container, accommodating smear slides 11; and smear transfer part 170. Smear transfer part 170 picks, picks up, takes out, grips or lifts smear slide 11 accommodated in slide magazine 90 transported by smear-container transport part 140, and supplies smear slide 11 to the smear-image capture apparatus after smear slide 11 thus taken out is put in transport case 152 to be described later.

In this embodiment, smear-container transport part 140 has two rows of front and rear transport units, that is, first transport unit 141 (first transport part) located on a rear side of smear transporting apparatus 100 and second transport unit 142 (second transport part) located in front of first transport unit 141. Each of first transport unit 141 and second transport unit 142 includes a belt conveyor including belts 143 and driver 144 which drives these belts 143. First transport unit 141 and second transport unit 142 transport slide magazines 90 in an X2 direction (see FIGS. 1 and 9).

As illustrated in FIG. 1, first transport unit 141 and second transport unit 142 can be divided into four regions according to the state of slide magazine 90. Specifically, first transport unit 141 and second transport unit 142 can be divided into: magazine buffer region 131 as a first supply region, magazine set region 132 as a second supply region, first magazine storage region 133 as a first storage region, and second magazine storage region 134 as a second storage region. Among these four regions, magazine set region 132 and second magazine storage region 134 belong to second transport unit 142. Meanwhile, magazine buffer region 131 and first magazine storage region 133 belong to first transport unit 141. First magazine storage region 133 and second magazine storage region 134 constitute a storage for storing slide magazines 90 which serve as the smear containers.

After smear preparing apparatus 10 completes the smearing process, smear slides 11 are stored in slide magazine 90 serving as a first smear container. Traverse transfer unit 130 transfers the slide magazine to magazine buffer region 131. First magazine storage region 133 is a region that stores slide magazine 90 as the first smear container which stores only smear slides 11 to be visually tested under a microscope, and from which smear slides 11 whose images are to be captured by smear-image capture apparatus 200 have been picked up. Magazine set region 132 is a region where empty slide magazines 90 set by the user are disposed. Second magazine storage region 134 is a region that stores slide magazine 90 storing smear slides 11 whose images have been captured by smear-image capture apparatus 200. Note that, in this embodiment, interrupting-smear-container set region 135 which is accessible to the user, and in which slide magazine 90 accommodating smear slide 11 prepared by this the user is set is located at a left side portion in magazine buffer region 131. Specifically, on a transport path where smear containers are transported, interrupting-smear-container set region 135 is located between magazine buffer region 131 where smear containers from smear preparing apparatus 10 are received and a position where an identification-information acquisition part to be described later acquires identification information.

Second transport unit 142 transports empty slide magazine 90 serving as a second smear container, which the user sets in magazine set region 132, to smear storage position A. Smear slides 11 whose images have been captured by smear-image capture apparatus 200 are sequentially accommodated in slide magazine 90 as the second smear container at this smear storage position A. When slide magazine 90 at smear storage position A is filled, second transport unit 142 transports slide magazine 90 filled with smear slides 11 from smear storage position A to second magazine storage region 134. Then, second transport unit 142 transports empty slide magazine 90 positioned on a left end of magazine set region 132 to smear storage position A.

On the other hand, first transport unit 141 transports, to smear pickup position P, slide magazine 90 as the first smear container which is received from smear preparing apparatus 10 and disposed in magazine buffer region 131. At this smear pickup position P, handling member 120 of smear transfer part 170 sequentially picks up smear slides 11 as described later. Smear slides 11 thus picked up are sorted into smear slides 11 whose images are to be captured by smear-image capture apparatus 200, and smear slides 11 whose images are not to be captured by smear-image capture apparatus 200. After the sorting of smear slides 11 is completed, slide magazine 90 is transported from smear pickup position P to first magazine storage region 133. Slide magazine 90 positioned at first magazine storage region 133 stores only smear slides 11 whose images are not to be captured by smear-image capture apparatus 200. These smear slides 11 are to be visually tested under a microscope.

In this embodiment, slide magazine 90 accommodating smear slides 11 is transported from smear preparing apparatus 10 to smear pickup position P. Smear slides 11 include ones whose images are to be captured by smear-image capture apparatus 200, and ones whose images are not to be captured. Hence, slide magazine 90 transported to smear pickup position P normally contains a mixture of the two types of smear slides 11. Nevertheless, in this embodiment, even if slide magazine 90 contains such a mixture, smear slides 11 whose images have been captured by smear-image capture apparatus 200 and smear slides 11 whose images are not captured by smear-image capture apparatus 200 are accommodated in different slide magazines 90, that is, slide magazine 90 as the first smear container and slide magazine 90 as the second smear container. Then, these slide magazines are stored in different regions. To enhance the resolution when an image is captured by smear-image capture apparatus 200, an immersion oil is applied to a sample such as blood smeared on smear slide 11 in some cases. Since smear slides 11 whose images have been captured are accommodated in slide magazine 90 different from slide magazine 90 accommodating smear slides 11 whose image has yet to be captured, this makes it possible to suppress the immersion oil contamination of smear slides 11 whose images have yet to be captured. Thus, when smear slide 11 whose image is not to be captured is visually observed, the user can visually observe smear slide 11 not contaminated with the oil by taking out slide magazine 90 accommodating the smear slide from first magazine storage region 133, thereby enhancing smear slide 11 handleability.

Slide magazine 90 positioned in second magazine storage region 134 stores smear slides 11 whose images have been captured by smear-image capture apparatus 200. As described above, since an immersion oil is sometimes applied to smear slide 11 when an image is captured, the oil applied to smear slide 11 may adhere to slide magazine 90. For this reason, it is desirable to divide slide magazines 90 used in the front-side row from slide magazines 90 used in the rear-side row. It is desirable to use slide magazines 90 which have a possibility of the oil contamination in the front-side row, and use slide magazines 90 which have no possibility of the oil contamination in the rear-side row. In this case, slide magazines 90 to be set in magazine set region 132 are slide magazines 90 storing smear slides 11 after image capturing, disposed in second magazine storage region 134, and then emptied by completing the processing on these smear slides 11. On the other hand, slide magazines 90 positioned in first magazine storage region 133 and then emptied by taking out smear slides 11 having been stored for the visual test under a microscope are set in introduction section D of magazine carry-in path 92 of smear preparing apparatus 10. Using slide magazines 90 differently in this manner makes it possible to efficiently clean these slide magazines 90. Specifically, slide magazines 90 disposed in second magazine storage region 134 are desirably set to be cleaned frequently because the possibility of the oil contamination is high. On the other hand, slide magazines 90 disposed in first magazine storage region 133 can be set to be cleaned less frequently because the slide magazines have no possibility of the oil contamination. Slide magazines 90 used in the front-side row can be easily distinguished from slide magazines 90 used in the rear-side row, for example, by changing the colors or in other ways.

As described above, magazine buffer region 131 in this embodiment has interrupting-smear-container set region 135, which is a region accessible to the user. Interrupting-smear-container set region 135 is located in a region at the left end portion in magazine buffer region 131, that is, a region at smear pickup position P side in magazine buffer region 131. Interrupting-smear-container set region 135 is a region where no slide magazine 90 is normally present. After smear preparing apparatus 10 supplies slide magazines 90 to magazine buffer region 131, first transport unit 141 sequentially transports slide magazines 90 to the left, that is, toward smear pickup position P.

Nevertheless, the user may manually prepare smear slide 11 instead of smear preparing apparatus 10 to capture an image with smear-image capture apparatus 200 for the analysis. To prepare smear slide 11 with smear preparing apparatus 10, a certain amount of a sample is required. However, it may be difficult to collect the certain amount of a sample from such a subject as an infant, for example. In such a case, smear preparing apparatus 10 cannot automatically prepare smear slide 11. As a result, the user manually prepares smear slide 11 using a sample collected from a subject. Moreover, it is also conceivable that when a sample needs to be analyzed quickly using smear-image capture apparatus 200, the user manually prepares smear slide 11 using a sample collected from a subject.

Interrupting-smear-container set region 135 is a region where slide magazine 90 accommodating smear slide 11 manually prepared as described above is set. First transport unit 141 transports slide magazine 90 set in interrupting-smear-container set region 135 to smear pickup position P.

Interrupting-smear-container set region 135 is normally set such that no slide magazine 90 is present so as to set slide magazine 90 accommodating manually-prepared smear slide 11 in interrupting-smear-container set region 135.

Figure 6:
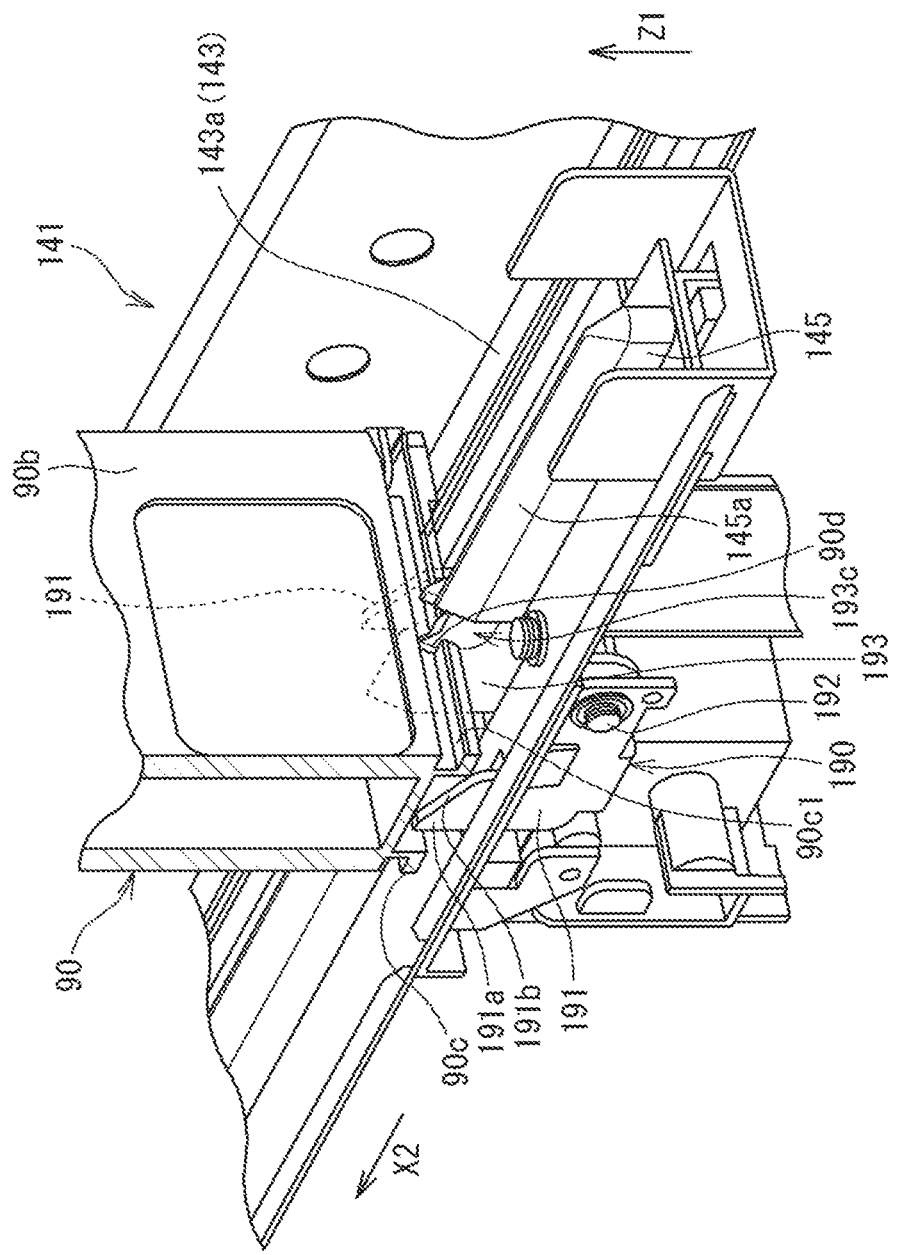
FIG. 6 is an explanatory perspective view of principal components of a first transport part.

FIG. 6 is an explanatory partial perspective view of first transport unit 141 positioned in interrupting-smear-container set region 135. As described above, first transport unit 141 includes a belt conveyor including belts 143 and driver 144 which drives these belts 143 (see FIG. 9). Belts 143 are provided in pair along the transport direction (X2 direction) of slide magazine 90. In FIG. 6, only one belt (rear-side belt) 143a is illustrated to facilitate the understanding. Substantially at the center in a width direction of the pair of belts 143, guide rail 145 is provided which guides the movement of slide magazine 90. Tip end portion 145a, which is an end portion in an upward direction (Z1 direction) of guide rail 145, has a tapered shape. In more details, the shape of a traverse cross section of tip end portion 145a is triangular, and corresponds to triangular notch 90d formed in base 90c of slide magazine 90 described above. Slide magazine 90 is transported while guided by this tip end portion 145a of guide rail 145 with tip end portion 145a being fitted in notch 90d of base 90c.

Detector 190 is provided within the pair of belts 143 in the width direction. Detector 190 has a pair of plate-shaped swing pieces 191. Swing pieces 191 are provided within the pair of belts 143 in the width direction. Swing pieces 191 are swingable about the same shaft 192. Tip end portion 191a, which is an end portion in an upward direction (Z1 direction) of each of swing pieces 191, has inclination surface 191b ascending in transport direction X2 of slide magazine 90. In a state not in contact with slide magazine 90, swing pieces 191 are biased by an unillustrated spring such that tip end portions 191a are directed upward (see FIG. 6).

Detector 190 is provided at a position immediately before interrupting-smear-container set region 135 when seen in transport direction X2 of slide magazine 90.

Figure 7:
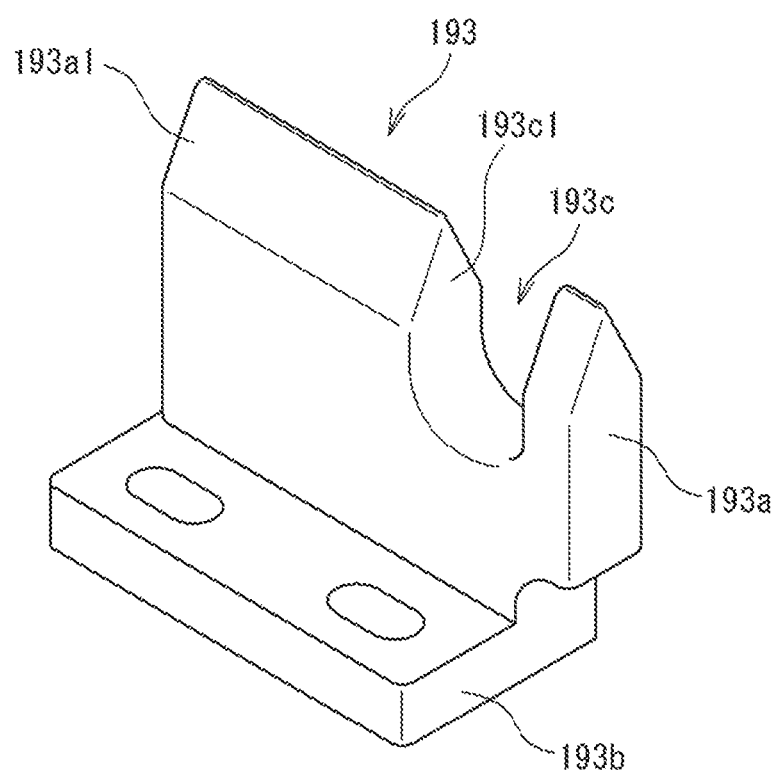
FIG. 7 is an explanatory perspective view of a stopper.

At a middle position between paired plate-shaped swing pieces 191 (middle position in the width direction of belts 143), stopper 193 is provided which is capable of stopping the movement of slide magazine 90. As illustrated in FIG. 7, stopper 193 includes main body 193a with a shape partially cut along a longitudinal direction of guide rail 145, and base 193b extending in the width direction of belts 143 from a bottom end of main body 193a. The shape of a traverse cross section of tip end portion 193a1, which is an end portion in an upward direction (Z1 direction) of main body 193a, has the same tapered shape as tip end portion 145a of guide rail 145. Normally, stopper 193 and guide rail 145 are positioned substantially on the same straight line. Accordingly, tip end portion 193a1 of main body 193a of stopper 193 is fitted in notch 90d of slide magazine 90, so that this slide magazine 90 can pass through the top of this stopper 193 without being interrupted by stopper 193. Notch 193c is formed in main body 193a of stopper 193. Notch 193c is formed at such a position that notch 193c is slightly shifted to an end portion from the center in a longitudinal direction of main body 193a. Notch 193c is formed to a size sufficient to accommodate long frame 90c1 of base 90c of slide magazine 90.

When slide magazine 90 passes through swing pieces 191, long frame 90c1 at a leading side of base 90c of slide magazine 90 comes into contact with inclination surfaces 191b of swing pieces 191, and thereby pushes these swing pieces 191 downward against the biasing force of the aforementioned spring. When long frame 90c1 at the leading side of base 90c passes through inclination surfaces 191b of swing pieces 191, the contact state between this long frame 90c1 and inclination surfaces 191b ends. Hence, swing pieces 191 return to the original position, that is, to the state where tip end portions 191a are directed upward, by the action of the spring. In this event, tip end portions 191a are located in recess 90e of base 90c of slide magazine 90. In addition, long frame 90c1 at a rear side of base 90c (the rear side in the transport direction (X2 direction) of base 90c) is located in notch 193c of stopper 193. From these states, when slide magazine 90 further moves toward smear pickup position P, long frame 90c1 at the rear side of base 90c comes into contact with inclination surfaces 191b of swing pieces 191, and thereby pushes these swing pieces 191 downward. Then, slide magazine 90 further moves toward smear pickup position P, and long frame 90c1 at the rear side of base 90c passes through inclination surfaces 191b of swing pieces 191, so that the contact state between long frame 90c1 and inclination surfaces 191b ends. As a result, swing pieces 191 return to the original position, that is, to the state where tip end portions 191a are directed upward, by the action of the spring. In this manner, swing pieces 191 swing up and down twice every time one slide magazine 90 passes through these swing pieces 191. Whether swing pieces 191 are in the state of being pushed downward or in the state where tip end portions 191a thereof are directed upward can be detected with, for example, an optical sensor, a microswitch, or the like.

Figure 8:
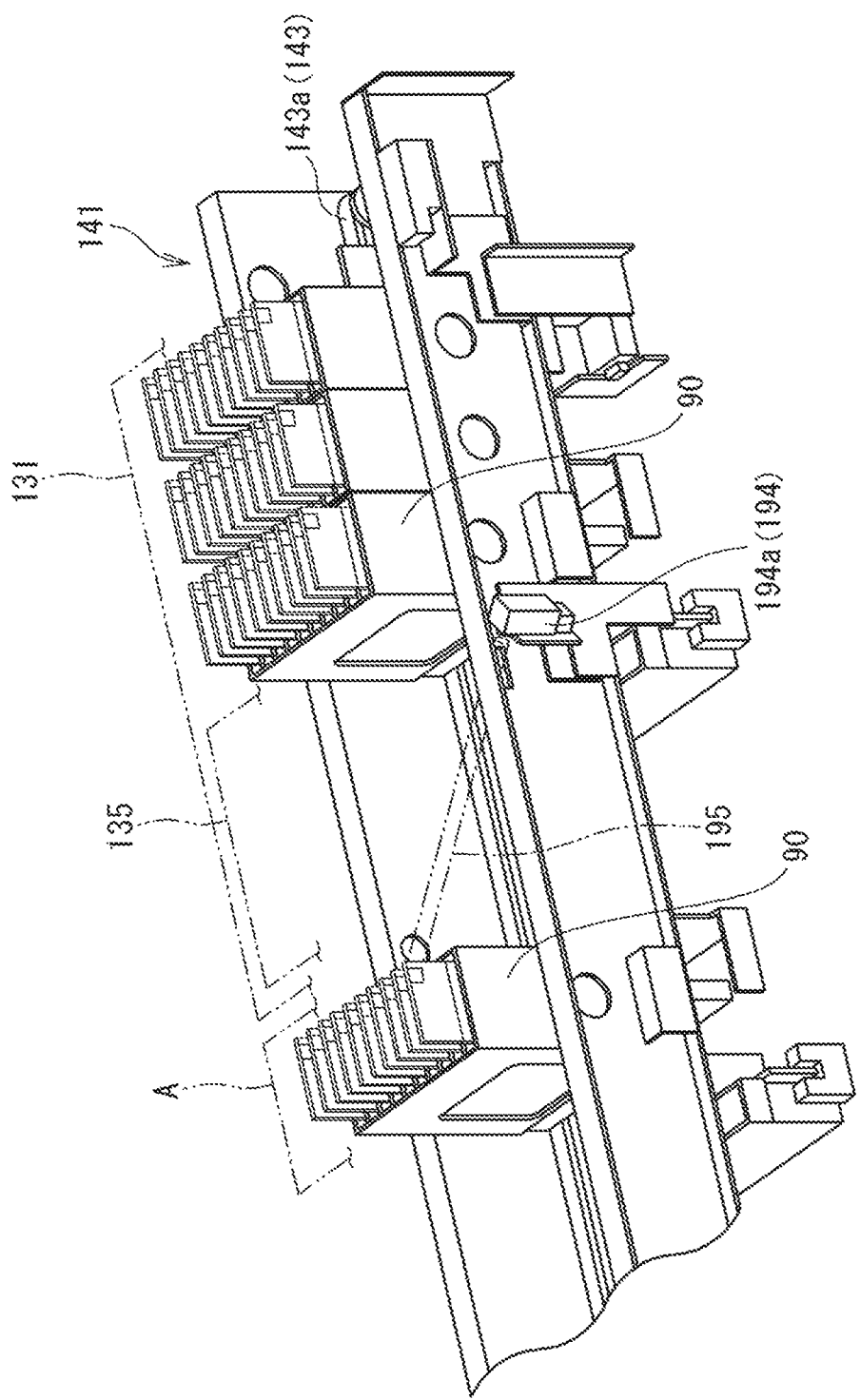
FIG. 8 is an explanatory perspective view of the first transport part including an interrupting-smear-container set region.

The operation of stopping slide magazine 90 by stopper 193 can be done as follows, for example. Controller 110 of smear transporting apparatus 100 can control such a stop operation. (1) Controller 110 determines whether or not swing pieces 191 once pushed downward is at the original position, that is, in the state where tip end portions 191a are directed upward (hereinafter, such a state is referred to as "neutral state"), by the action of the spring. In this neutral state, tip end portions 191a of swing pieces 191 are located in recess 90e of base 90c of slide magazine 90. If it is determined that swing pieces 191 are in the neutral state, controller 110 determines whether or not slide magazines 90 are positioned at smear pickup position P and interrupting-smear-container set region 135. At smear pickup position P also, the same sensor is provided as detector 190 having swing pieces 191 described above. A signal from such a sensor enables controller 110 to determine whether swing pieces 191 at smear pickup position P is in the neutral state or not. Until the sorting of smear slides 11 accommodated in slide magazine 90 is completed, this slide magazine 90 is stopped at smear pickup position P. On the other hand, optical sensor 194 is provided in interrupting-smear-container set region 135 as illustrated in FIG. 8. Light receptor 194a receives light beam 195 emitted from an unillustrated light emitter. Such light receptor 194a and light emitter constitute optical sensor 194. When slide magazine 90 accommodating smear slide 11 manually prepared by the user is disposed in interrupting-smear-container set region 135, slide magazine 90 blocks light beam 195 from the light emitter to light receptor 194a. This enables the detection that slide magazine 90 is present in interrupting-smear-container set region 135.

(2) If controller 110 determined that slide magazine 90 is positioned at any one of smear pickup position P and interrupting-smear-container set region 135, an unillustrated drive mechanism slides stopper 193 in the width direction of the pair of belts 143, that is, the Y direction (see FIG. 1). Sliding stopper 193 in this manner shifts the position of this stopper 193 from notch 90d of base 90c of slide magazine 90 in the width direction (Y direction). Hence, even if belts 143 are driven, edge surface 193c1a of notch 193c of stopper 193 touches long frame 90c1 at the rear side of slide magazine 90, so that stopper 193 stops the movement of slide magazine 90 in the transport direction.

The same mechanism as stopper 193 in magazine buffer region 131 is also provided at each of smear pickup position P and smear storage position A. Thus, when slide magazine 90 is supplied from smear preparing apparatus 10 to magazine buffer region 131, even if belts 143 are driven to transport slide magazine 90 toward smear pickup position P, belts 143 transport only slide magazine 90 positioned in magazine buffer region 131, while the stopper at smear pickup position P stops slide magazine 90 positioned thereat until the sorting of smear slides 11 accommodated in slide magazine 90 at smear pickup position P is completed. In other words, since this embodiment adopts the stopper described above, it is possible to transport only necessary slide magazine 90. Slide magazine 90 unnecessary to be transported keeps sliding on driving belts 143 while prohibited from moving by stopper 193.

Figure 9:
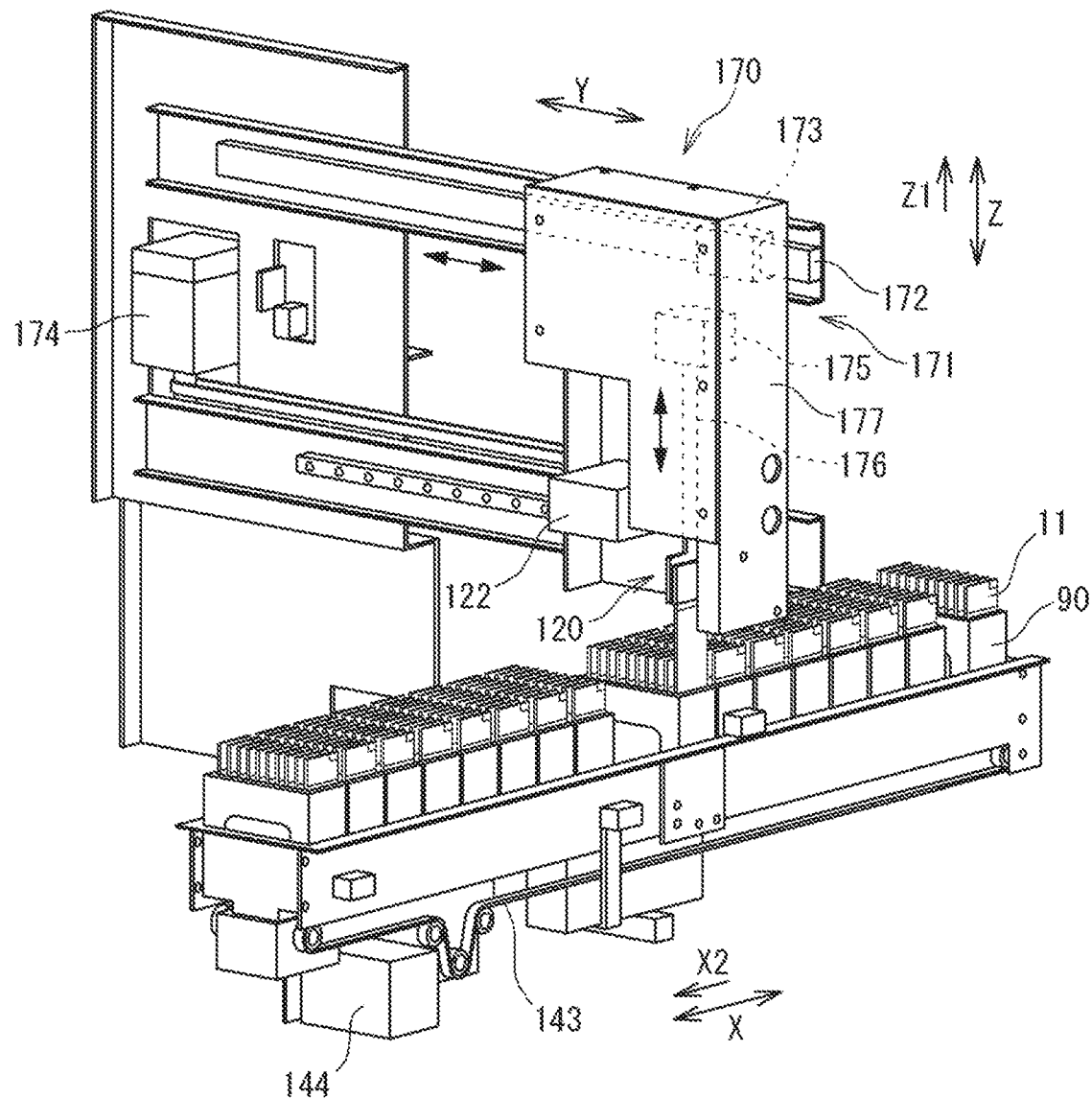
FIG. 9 is an explanatory perspective view of a smear transfer part

As illustrated in FIG. 9, smear transfer part 170 is provided above (Z1 direction) first transport unit 141 and second transport unit 142. Like transfer unit 30 in smear preparing apparatus 10 described above, smear transfer part 170 is provided to grip and transfer smear slide 11. Smear transfer part 170 is capable of putting each smear slide 11 one by one in and out slide magazine 90. As the configuration of smear transfer part 170 for putting each smear slide 11 in and out one by one in this manner, various configurations can be adopted. In this embodiment, as illustrated in FIG. 9, a 2-axis coordinate robot is adopted which is movable in the horizontal direction (Y direction) and in the top-bottom direction (Z direction) or vertical direction, and includes handling member 120 for gripping smear slide 11. As handling member 120, it is possible to use, for example, an open-close mechanism capable of grasping smear slide 11 from both sides, or an aspiration mechanism which grasps smear slide 11 by suction on a predetermined spot thereof at a negative pressure.

Smear transfer part 170 is movable in the horizontal direction (Y direction) by movement mechanism 171. Movement mechanism 171 includes Y-axis rail 172, Y-axis slider 173 which engages with this Y-axis rail 172, and Y-axis motor 174. As Y-axis motor 174, for example, stepping motors and servomotors can be adopted. Y-axis motor 174 moves Y-axis slider 173 in the Y direction with a transmission mechanism including a belt-pulley mechanism.

Smear transfer part 170 includes Z-axis motor 175 and transmission mechanism 176 for elevating and lowering handling member 120. Z-axis motor 175 is capable of elevating and lowering handling member 120 with transmission mechanism 176.

Figure 10:
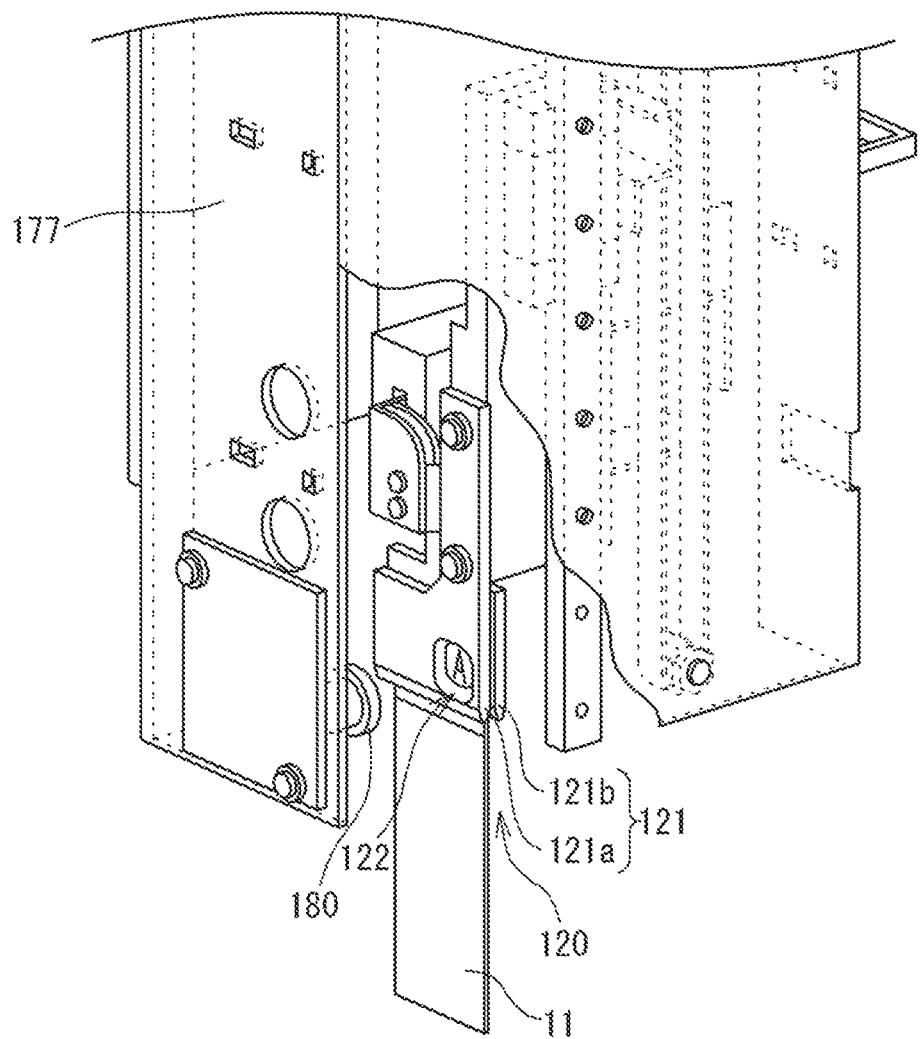
FIG. 10 is an explanatory perspective view of principal components of the smear transfer part illustrated in FIG. 9.

As illustrated in FIG. 10, handling member 120 includes a pair of gripping plates 121a, 121b. Handling member 120 is capable of gripping one smear slide 11 in the thickness direction from both sides with the pair of gripping plates 121a, 121b. The pair of gripping plates 121a, 121b grip smear slide 11 by respectively coming into contact with the front surface and the back surface of smear slide 11. Of the pair of gripping plates 121a, 121b, gripping plate 121b at the back surface side is capable of moving smear slide 11 in the thickness direction. Gripping plate 121b can be moved by motor 124. Note that, other than the motor, an actuator, for example, an air cylinder, a solenoid, or the like can also be used.

An opening 122 is formed in gripping plate 121a of the pair of gripping plates 121a, 121b which is at the front surface side (side where frost section 12 is provided) of smear slide 11. The position and shape of opening 122 formed are selected so that a camera to be described later can capture an image of image-capturing necessity identification information typed on frost section 12 of smear slide 11 gripped by the pair of gripping plates 121a, 121b. In this embodiment, substantially rectangular opening 122 is formed in gripping plate 121a at the front surface side of smear slide 11. The pair of gripping plates 121a, 121b grip a portion of frost section 12 of smear slide 11 excluding where image-capturing necessity identification information is typed.

Smear transporting apparatus 100 according to this embodiment further includes the identification-information acquisition part for acquiring identification information provided to smear slide 11 taken out by smear transfer part 170. As illustrated in FIG. 10, an inner surface of casing 177 accommodating mechanisms such as Z-axis motor 175 of smear transfer part 170 is provided with image capture part 180 which is the identification-information acquisition part. This image capture part 180 is provided at a position facing an identifier for whether image capturing is necessary or not of smear slide 11 taken up by handling member 120 of smear transfer part 170. As image capture part 180, for example, a camera can be used. As the identification-information acquisition part, a barcode reader may be used instead of image capture part 180.

Image capture part 180 is capable of capturing an image of image-capturing necessity identification information, which is exposed to the outside from opening 122 formed in gripping plate 121*a* at the front surface side of smear slide 11. In this embodiment, as the image-capturing necessity identification information, alphabet "A" is typed on frost section 12. This image-capturing necessity identification information "A" is exposed to the outside from opening 122. The captured image data is transmitted to controller 110 of smear transporting apparatus 100. On the basis of the transmitted image data, captured-image determination part 112 of controller 110 determines whether or not smear slide 11 taken up by handling member 120 is one whose image is to be captured by smear-image capture apparatus 200.

Figure 11:
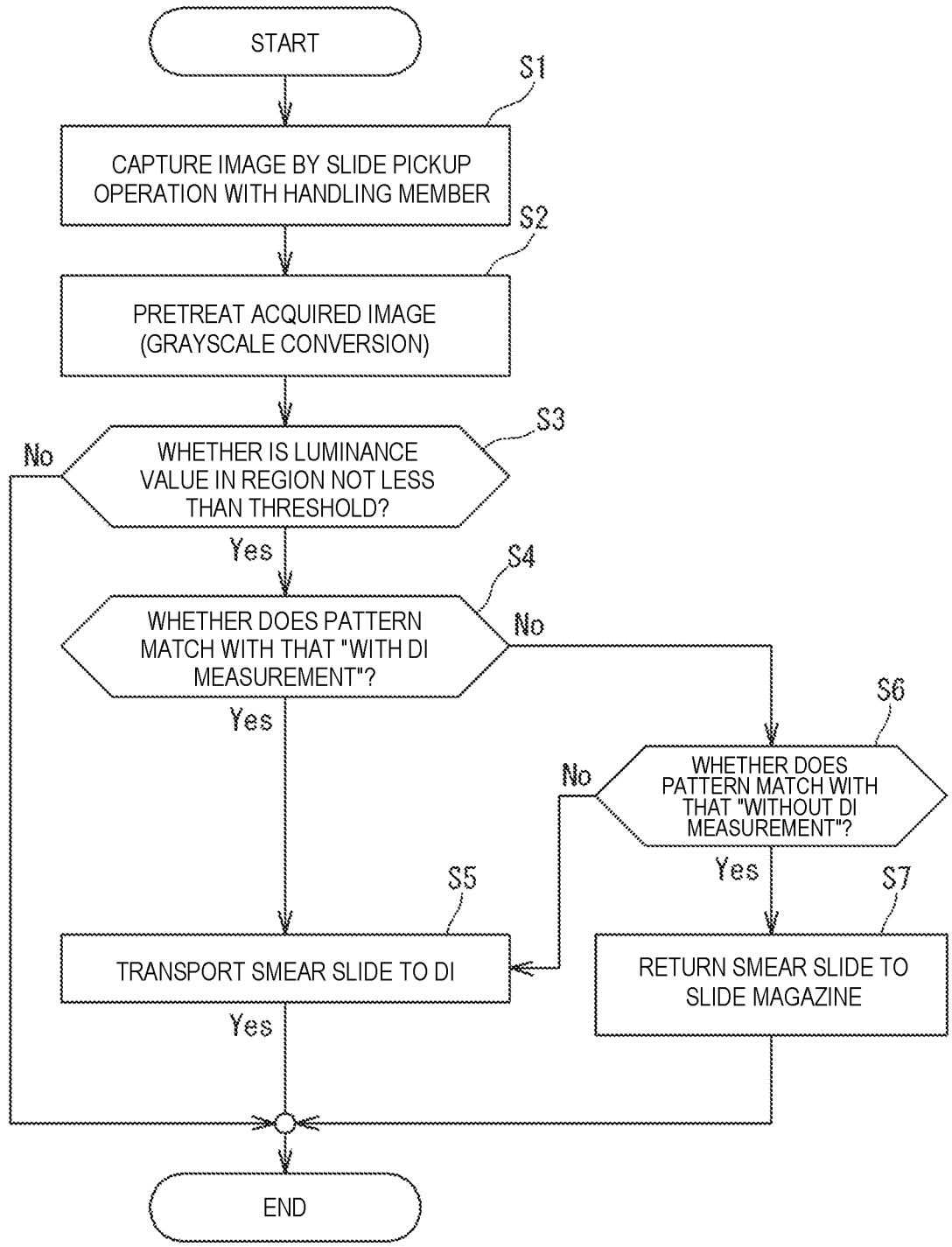
FIG. 11 is a flowchart for illustrating a procedure of determining whether a smear slide is one whose image is to be captured or not.

FIG. 11 is a flowchart for illustrating a procedure of determining whether smear 11 slide is one whose image is to be captured or not. First, in step S1, an image of frost section 12 of smear slide 11 taken up by handling member 120 from slide magazine 90 at smear pickup position P is captured. Image capture part 180 obtains such an image of smear slide 11 by capturing an image of frost section 12 exposed to the outside from opening 122 formed in gripping plate 121*a* at the front surface side of smear slide 11. The captured image is transmitted to controller 110 of smear transporting apparatus 100.

Subsequently, in step S2, controller 110 performs a gray-scale conversion as a pretreatment on the acquired image. In this embodiment, it is determined not only whether image capturing by smear-image capture apparatus (DI) 200 is necessary or not, but also whether handling member 120 grips smear slide 11 or not. In a case where hand member 31 of smear preparing apparatus 10 fails to grip smear slide 11 or similar cases, it is conceivable that there is a space where no smear slide 11 is stored in a section of slide magazine 90. Moreover, in a case where an urgent visual test is necessary, it is conceivable that when the user pulls up smear slide 11 in the middle of the test, there is a similar space where no smear slide 11 is stored in a section of slide magazine 90.

Subsequently, in step S3, controller 110 determines whether or not a luminance value of a region in frost section 12 exposed to the outside through opening 122 is not less than a threshold saved in advance. Of the pair of gripping plates 121, gripping plate 121*b* at the back surface side of smear slide 11 has a surface which faces a surface of gripping plate 121*a* at the front surface side of smear slide 11, and which is colored with a color, for example, black, having a luminance value lower than a luminance value frost section 12 can take. The color may be dark brown or other colors than black. Hence, if image capture part 180 captures an image of a portion exposed from opening 122 with no smear slide 11 gripped by the pair of gripping plates 121, the obtained image has such a low luminance value. When image-capturing necessity identification information is typed on frost section 12 of smear slide 11, the portion of frost section 12 exposed to the outside through opening 122 where the image-capturing necessity identification information is typed is brighter than black. Thus, setting the threshold at a larger luminance value than the aforementioned low value and comparing this threshold with a luminance value to be obtained make it possible to determine whether smear slide 11 is present or absent. In step S3, if it is determined that the obtained luminance value is not less than the threshold, controller 110 advances the processing to step S4. On the other hand, if it is determined that the obtained luminance value is less than the threshold, controller 110 completes the determination procedure. In step S3, image processing is performed by utilizing the luminance value indicating the magnitude of brightness of the acquired mage. In step S3, if it is determined that no smear slide 11 is gripped, smear transfer part 170 can check the position using, for example, a rotary encoder, and prepare transferring of the next smear slide 11 without returning to the original position of this smear transfer part 170.

In step S4, controller 110 performs pattern processing on the acquired image, and determines whether or not the pattern of this image matches with an image capturing pattern of smear-image capture apparatus (DI) saved in advance. If it is determined that the pattern of the acquired image matches with the image capturing pattern of the smear-image capture apparatus, controller 110 advances the processing to step S5, and transports smear slide 11 gripped by handling member 120 to smear-image capture apparatus 200. On the other hand, if it is determined that the pattern of the acquired image does not match with the image capturing pattern of the smear-image capture apparatus, controller 110 advances the processing to step S6.

In step S6, controller 110 determines whether or not the pattern of the acquired image matches with a non-image capturing pattern of the smear-image capture apparatus saved in advance. If it is determined that the pattern of the acquired image matches with the non-image capturing pattern of the smear-image capture apparatus, controller 110 advances the processing to step S7, and returns smear slide 11 gripped by handling member 120 to the original position in slide magazine 90. On the other hand, if it is determined that the pattern of the acquired image does not match with the non-image capturing pattern of the smear-image capture apparatus, controller 110 advances the processing to step S5, and transports smear slide 11 gripped by handling member 120 to smear-image capture apparatus 200. In this embodiment, since smear slide 11 manually prepared by the user is also desirably subjected to the processing by smear-image capture apparatus 200, if whether image-capturing necessity identification information is either information indicating that image capturing is necessary or information indicating that image capturing is unnecessary is unknown, smear-image capture apparatus 200 ought to capture an image. This is because when the user manually prepares smear slide 11, frost section 12 may not be typed, or patient information may be written with a pencil or the like. As described above, since smear slide 11 whose pattern does not match with the non-image capturing pattern is transported to smear-image capture apparatus 200, the processing in step S4 may be omitted.

When it is determined that smear slide 11 is one whose image is to be captured by smear-image capture apparatus 200, smear transfer part 170 transfers the smear slide to smear delivery position W to be described later, and horizontal movement mechanism 123 constituting this smear transfer part 170 transports the smear slide to smear-image capture apparatus 200.

As illustrated in FIG. 1, horizontal movement mechanism 123 is a mechanism for moving smear slide 11 in the right-left direction between smear delivery position W and smear receiver 205 of smear-image capture apparatus 200. Horizontal movement mechanism 123 includes transport unit 150 which receives smear slide 11 from smear transfer part 170 at smear delivery position W, moves in the left direction toward smear receiver 205 of smear-image capture apparatus 200, receives smear slide 11 whose image has been captured from smear receiver 205, and moves in the right direction toward smear delivery position W.

Figure 12:
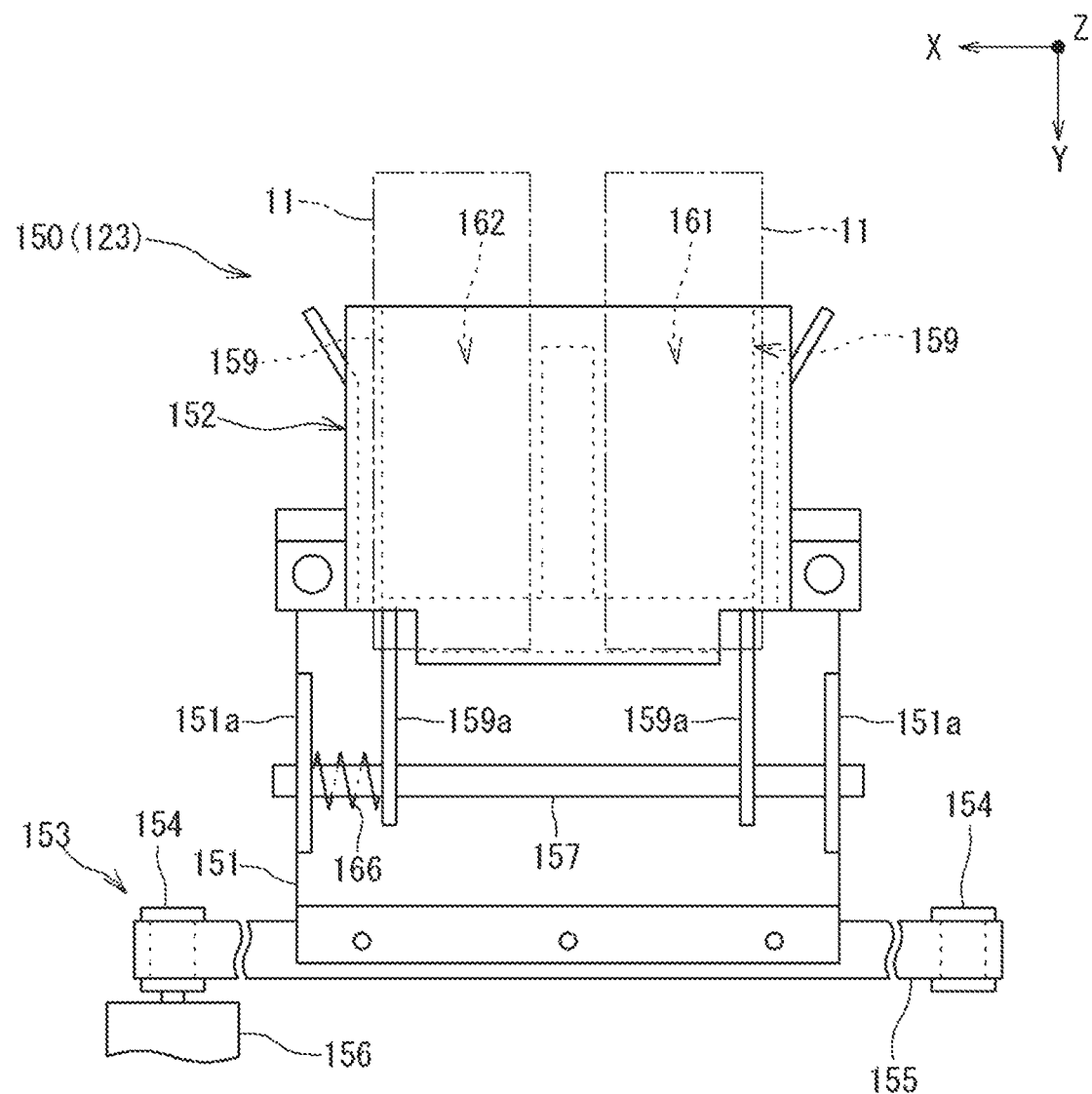
FIG. 12 is a plan explanatory diagram of a horizontal movement mechanism.

As illustrated in FIG. 12, transport unit 150 includes base 151, transport case 152, and traverse movement part 153. An apparatus frame (unillustrated) of smear transporting apparatus 100 supports base 151 movably in the right-left direction between smear delivery position W illustrated in FIG. 1 and smear receiver 205 of smear-image capture apparatus 200. Traverse movement part 153 includes a belt conveyor including belt 155 wound around a pair of right and left pulleys 154, drive motor 156 which drives one of pulleys 154, and so forth. Moreover, in an upper portion of base 151, a pair of right and left support pieces 151a are provided. Support shaft 157 having an axis in the right-left direction is bridged between these support pieces 151a.

Transport case 152 functions as a container formed in accordance with the shape of smear slides 11 in such a manner as to accommodate these smear slides 11. Transport case 152 includes first smear accommodation section 161 which accommodates smear slide 11 whose image has yet to be captured, and second smear accommodation section 162 which accommodates smear slide 11 whose image has been captured. Right and left wall members 159 of transport case 152 are respectively provided with link arms 159a extending frontward. Tip end portions of link arms 159a are rotatably linked to support shaft 157. Thus, transport case 152 is swingable up and down (back and forth) around support shaft 157. This swinging can change the posture between a horizontal posture (reference posture) in which openings of first, second smear accommodation sections 161, 162 are directed rearward and a standing posture in which the openings are directed upward. In other words, transport case 152 is capable of changing the posture between a state where the smeared surface of smear slide 11 is directed in a substantially perpendicular direction (horizontal posture in which smear slide 11 is substantially horizontal) and a state where the smeared surface is directed in the horizontal direction (one direction intersecting with the perpendicular direction) (standing posture).

As illustrated in FIGS. 13A to 14B, posture change mechanism 165 changes the posture of transport case 152 of transport unit 150. This posture change mechanism 165 includes operation bar 165a inserted below transport case 152 of transport unit 150 positioned at smear delivery position W, and driver 165b as a rotation mechanism which moves or rotates this operation bar 165a up and down. Driver 165b can be constituted of a drive motor, a link member, and so forth. Moreover, when driver 165b moves operation bar 165a, transport case 152 swings or rotates up and down around support shaft 157, and is in any one posture of horizontal posture and standing posture described above. Note that, to support shaft 157, bias member 166 including a torsion coil spring (see FIG. 12) is attached. This bias member 166 biases transport case 152 in a direction in which the transport case swings downward (direction to be in the horizontal posture).

Smear slide 11 pulled up from slide magazine 90 by handling member 120 of smear transfer part 170 is inserted into first smear accommodation section 161 of transport case 152 of transport unit 150 at smear delivery position W by lowering handling member 120. In this event, posture change mechanism 165 makes transport case 152 in the standing posture while the openings of first smear accommodation section 161 and of second smear accommodation section 162 are directed upward.

Figure 13A:
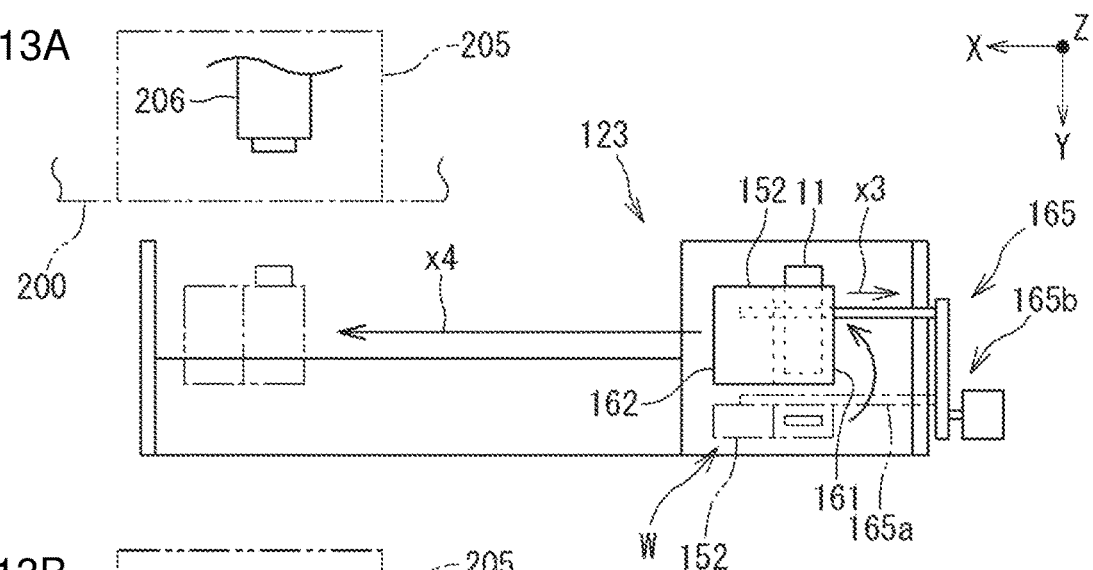
FIGS. 13A to 13C are diagrams for explaining operations of the horizontal movement mechanism.
Figure 13B:
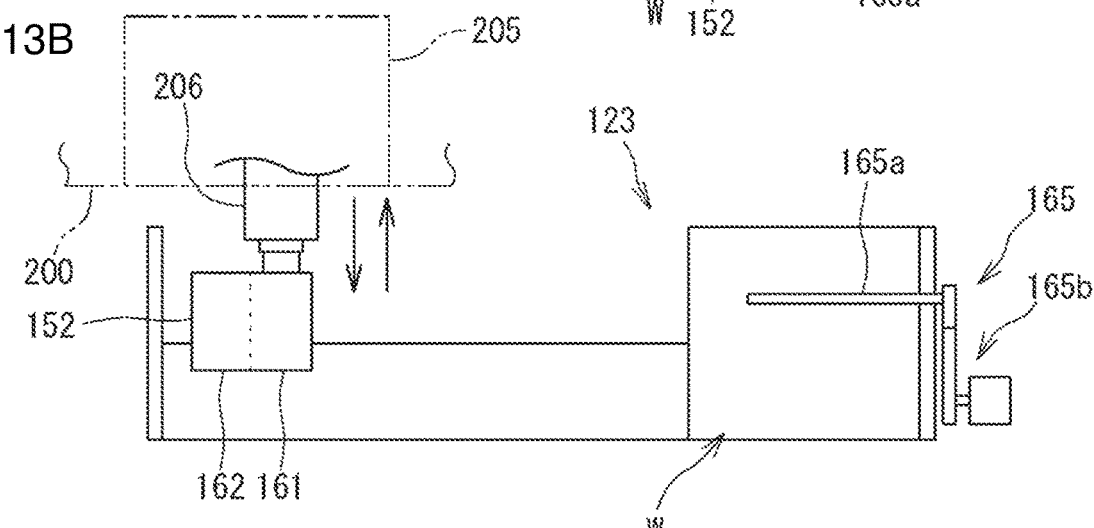
Figure 13C:
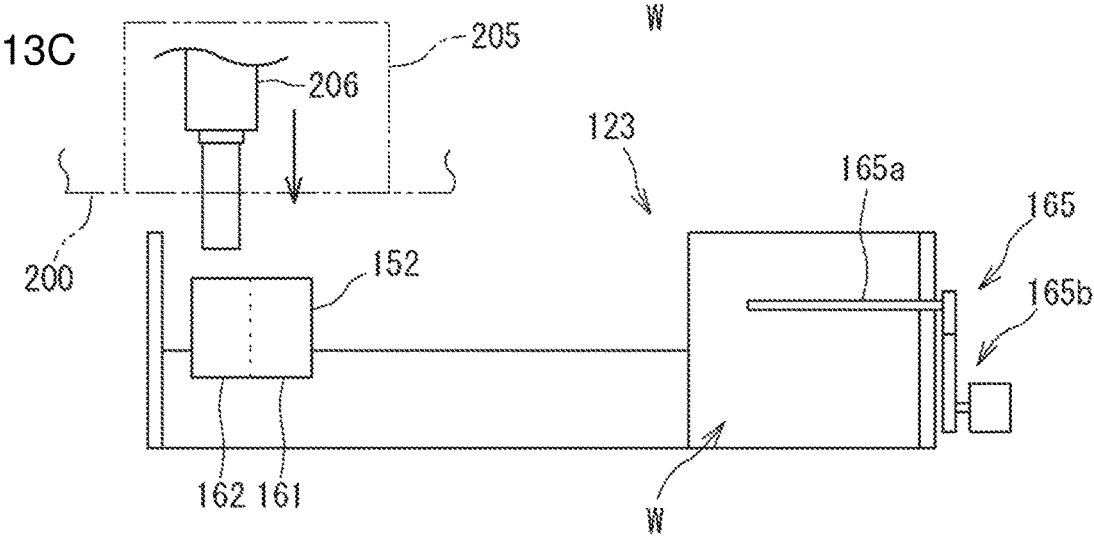
Figure 14A:
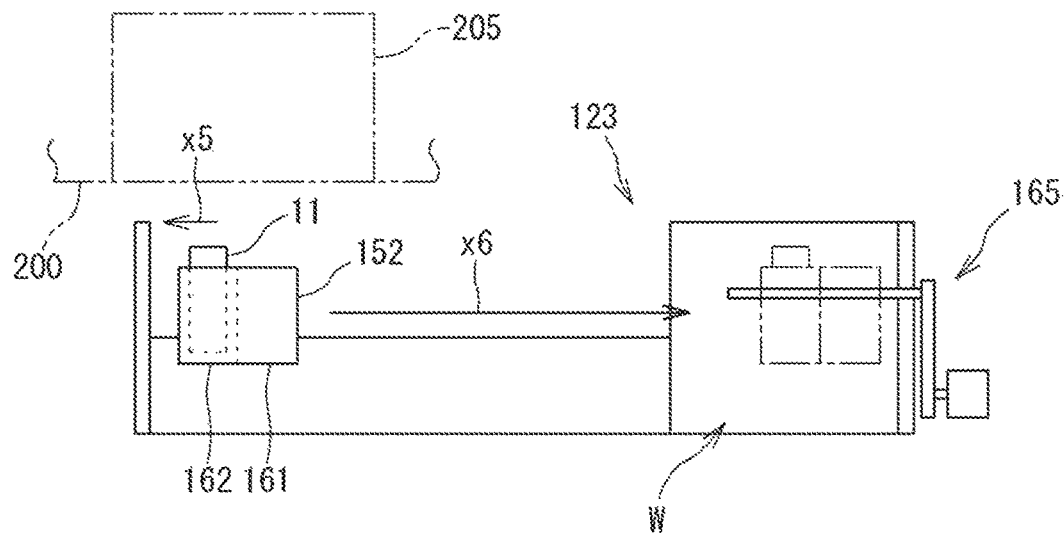
FIGS. 14A and 14B are diagrams for explaining operations of the horizontal movement mechanism.
Figure 14B:
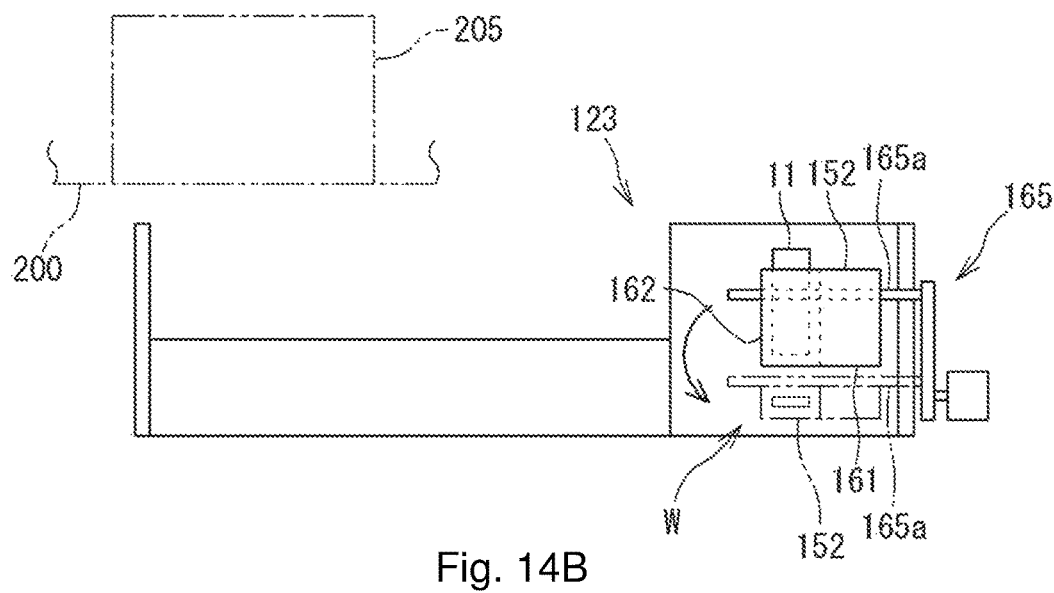
Figure 15:
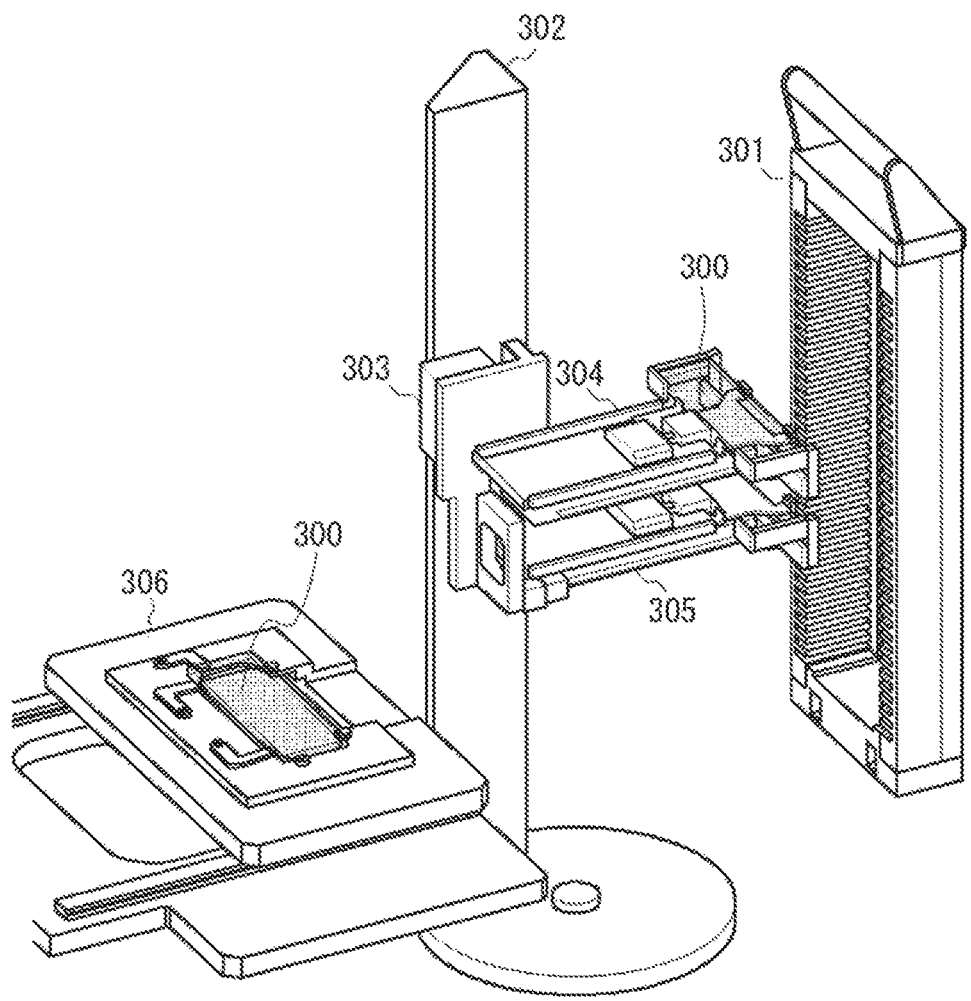
FIG. 15 is a plan explanatory diagram of a conventional smear preparing apparatus.

As illustrated in FIGS. 13A to 13C, when smear slide 11 is inserted in transport case 152 of transport unit 150 at smear delivery position W and posture change mechanism 165 changes the posture of transport case 152 to the horizontal posture, traverse movement part 153 (see FIG. 12) is activated to move transport case 152 accommodating smear slide 11 in the left direction (arrow x4). Thereby, transport case 152 is positioned at smear receiver 205 of smear-image capture apparatus 200 (see FIG. 13A).

Smear-image capture apparatus 200 includes transport unit 206 for moving smear slide 11. This transport unit 206 takes out smear slide 11 from transport case 152 moved to smear receiver 205 (see FIG. 13B). Transport unit 206 transports smear slide 11 thus taken out to oil applier 207. This oil applier 207 applies as necessary an oil to a sample such as blood smeared on this smear slide 11. Then, transport unit 206 transports smear slide 11 to image capture part 201 (see FIG. 1). This image capture part 201 captures an image of the sample. The captured image data is transmitted to controller 202. Controller 202 performs predetermined processings such as cell-characteristic extraction processing, identification classification processing, blood-cell image trimming, blood-cell automatic classification, and counting each blood cell type. The captured image data and the analysis result can be displayed on display monitor 203, or can be outputted with an unillustrated printer or the like. Controller 202 is connected to controller 110 of smear transporting apparatus 100 with communicators 204, 111, and information exchange is possible for operations in collaboration with each other.

Transport unit 206 returns smear slide 11 whose image has been captured (tested) to smear receiver 205, which then returns the smear slide to awaiting transport case 152. In this event, smear slide 11 whose image has been captured is inserted in second smear accommodation section 162 of transport case 152 (see FIG. 13C). Subsequently, transport case 152 is transported in the right direction (arrow x6) (see FIG. 14A) and positioned at smear delivery position W again. Thereafter, posture change mechanism 165 changes the posture of transport case 152 of transport unit 150 from the horizontal posture to the standing posture (see FIG. 14B).

Handling member 120 of smear transfer part 170 takes up smear slide 11 in second smear accommodation section 162 of transport case 152 in the standing posture at smear delivery position W, and stores the smear slide in slide magazine 90 awaiting at smear storage position A.

Note that, in the operation example of transport case 152 explained using FIGS. 13A to 14B, transport case 152 moved to smear receiver 205 of smear-image capture apparatus 200 awaits at the position after delivering smear slide 11 to transport unit 206 until transport unit 206 transports smear slide 11 whose image has been captured (see FIGS. 13B and 13C). The image capturing of smear slide 11 by smear-image capture apparatus 200 and the analysis normally need approximately 2 minutes. Hence, when smear slide 11 is delivered to transport unit 206, immediately thereafter making transport case 152 return to smear delivery position W, receive smear slide 11 to be analyzed the next at this smear delivery position W, and return transport case 152 to smear receiver 205 can shorten the waiting time and enhance the analysis efficiency. In this case, first, transport unit 206 places smear slide 11 whose image has been captured in second smear accommodation section 162 of transport case 152 waiting at smear delivery position W. Subsequently, transport unit 206 takes out smear slide 11 to be analyzed the next in first smear accommodation section 161 of transport case 152.

Other Modification Examples

The invention is not limited to the above-described embodiments, and various modifications are possible within the scope of the claims.

For example, in the above-described embodiment, the captured-image determination part of the smear transporting apparatus determines whether or not a smear slide is one whose image is to be captured by the smear-image capture apparatus. Nonetheless, it is also possible to make the host computer determine whether or not a smear slide is one whose image is to be captured by the smear-image capture apparatus by transmitting image data captured by the image capture part of the smear transporting apparatus to this host computer.

Moreover, in the above-described embodiment, if it is determined that a smear slide taken up by the handling member from a slide magazine is one whose image is not to be captured, the smear slide is returned to the original slide magazine. Nonetheless, such a smear slide can be accommodated in another slide magazine different from the original slide magazine. This another slide magazine may be disposed in the first magazine storage region from the beginning, or may be moved to the first magazine storage region after a predetermined number of smear slides are determined to be ones whose images are not to be captured and accommodated together.

Further, in the above-described embodiment, the printer of the smear preparing apparatus types or prints identification information on a smear slide. Nonetheless, the invention is not limited thereto. Identification information may be provided to a smear slide in other ways. For example, the color of a smear slide whose image is to be captured can be changed from the color of a non-image-capturing-target smear slide whose image is not to be captured. In this case, the color itself constitutes identification information. Alternatively, instead of using the typing unit of the smear preparing apparatus, a smear slide printed in advance with identification information on whether image capturing is necessary or not can be used. Furthermore, in a case other than typing on a smear slide, a seal or the like on which identification information is typed can also be pasted to a smear slide.

Furthermore, in the above-described embodiment, a slide magazine accommodating smear slides whose images have been captured and a slide magazine accommodating smear slides whose images are not to be captured are respectively stored in different magazine storage regions. Nevertheless, it is only necessary that smear slides whose images have been captured and smear slides whose images are not to be captured should be accommodated in different slide magazines. The slide magazine accommodating smear slides whose images have been captured and the slide magazine accommodating smear slides whose images are not to be captured may be stored in the same magazine storage region.

Note that, in the above-described embodiments, a smear slide is pulled out, picked, picked up, taken out, gripped or lifted from a slide magazine, and after the image capturing by the smear-image capture apparatus is completed, the smear slide passes above the original slide magazine and is accommodated in a different slide magazine. To prevent the immersion oil from dropping onto or into the original slide magazine from the smear slide whose image has been captured when the smear slide whose image has been captured passes above the slide magazine, a cover may be provided over the slide magazine. For example, a link mechanism may be provided in which the cover moves away from the top of the slide magazine in the horizontal direction when the handling member is lowered to pull out a smear slide from the slide magazine, and the cover moves to approach right above the slide magazine when the handling member gripping the smear slide is elevated from the slide magazine.

Figure 16:
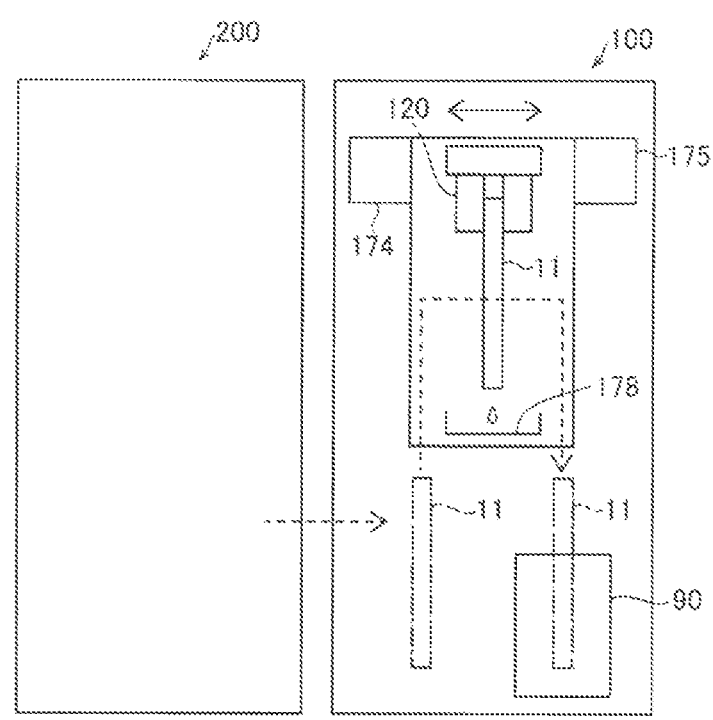
FIG. 16 is a schematic view of a smear transporting apparatus.

Specifically, as illustrated in FIG. 16, embodiments may include smear transporting apparatus 100.

As illustrated in FIG. 16, smear transporting apparatus 100 includes handling member 120 (handling part) and liquid receiver 178. Smear transporting apparatus 100 also includes Y-axis motor 174 and Z-axis motor 175. Handling member 120 is moved by Y-axis motor 174 and Z-axis motor 175 and holds and transports smear slide 11 whose image has been captured by smear-image capture apparatus 200 to slide magazine 90 configured to accommodate smear slide 11. Liquid receiver 178 is placed under or directly below handling member 120, is moved by Y-axis motor 174 and Z-axis motor 175 with handling member 120, and receives liquid dropped from smear slide 11. Since handling member 120 and liquid receiver 178 move together, liquid receiver 178 can receive, catch or collect liquid dropped from smear slide 11 during transferring of smear slide 11. Thus, it can prevent liquid dropped from smear slide 11 from adhering or attaching to the apparatus regardless of transportation paths of smear slide 11.

[Detailed Configuration of a Liquid Receiver]

Figure 17:
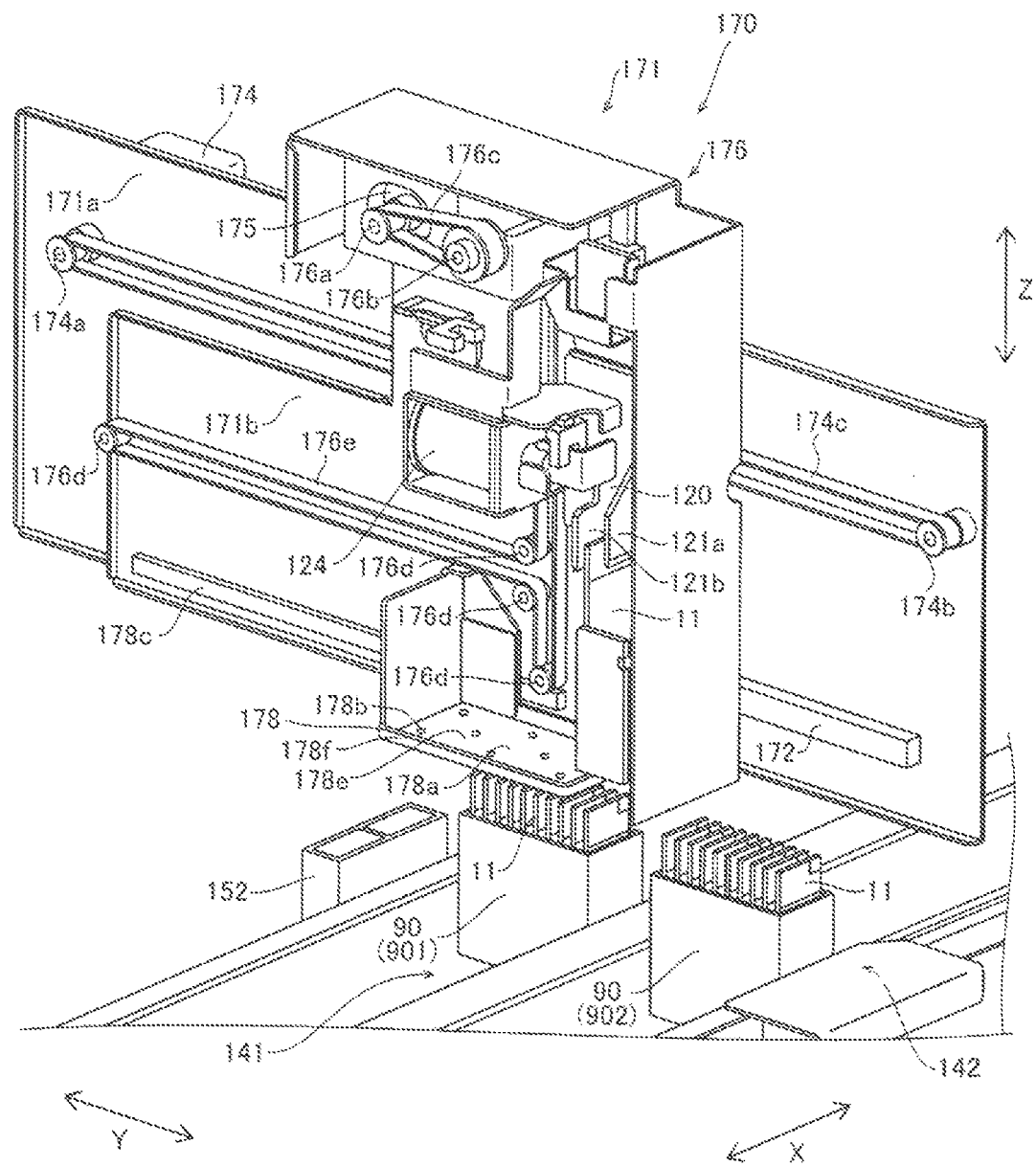
FIG. 17 is a schematic perspective view of the smear transporting apparatus.

The following explains in details a preferable embodiment configuration of liquid receiver 178 in smear transporting apparatus 100 illustrated in FIG. 16 referring to FIG. 17 and its subsequent figures.

As illustrated in FIG. 17, smear transporting apparatus 100 includes smear transfer part 170. Smear transporting apparatus 100 also includes movement mechanism 171, Y-axis rail 172, Y-axis slider 173 (see FIG. 18), Y-axis motor 174, Z-axis motor 175, transmission mechanism 176, and liquid receiver 178. Smear transfer part 170 includes handling member 120. Handling member 120 contains a pair of gripping plates 121a, 121b.

Transmission mechanism 176 includes pulleys 176a and 176b, belt 176c, pulleys 176d, and belt 176e. Liquid receiver 178 includes tray 178a. Tray 178a includes protruding part 178b. Rail 178c and slider 178d are provided to second support part 171b.

Handling member 120 holds and transports smear slide 11. Specifically, handling member 120 grips, holds and transports smear slide 11. Handling member 120 is capable of gripping one smear slide 11 in a thickness direction from both sides with the pair of gripping plates 121a, 121b. Handling member 120 also relatively moves the pair of gripping plates 121a, 121b with the drive of motor 124. Thus, as motor 124 drives, a facing distance between the pair of gripping plates 121a, 121b changes, which enables the pair of gripping plates 121a, 121b to grip or release smear slide 11. An actuator such as an air cylinder, a solenoid, or the like can be also used for motor 124. Smear slide 11 can be held in a different method of gripping; for example, smear slide 11 can be held by suction or by supporting from below.

Movement mechanism 171 includes first support part 171a and second support part 171b. First support part 171a is fixed to smear transporting apparatus 100. First support part 171a also supports second support part 171b being able to move horizontally. Specifically, first support part 171a sustains second support part 171b movable in a front-rear direction (Y direction). First support part 171a is in a shape of a flat plate on a vertical surface. Y-axis rail 172 and Y-axis motor 174 are attached to first support part 171a. Pulleys 174a and 174b, and belt 174c are provided to first support part 171a.

Second support part 171b can move in the Y direction along Y-axis rail 172. Specifically, Y-axis slider 173 in second support part 171b engages movably with Y-axis rail 172 to be movable. Second support part 171b moves in the Y direction along Y-axis rail 172 as Y-axis motor 174 drives. Thus, Y-axis motor 174's drive activates belt 174c. As belt 174c drives, second support part 171b attached to belt 174c shifts in the Y direction. Second support part 171b is in a shape of a flat plate on a vertical surface. Additionally, second support part 171b is provided with handling member 120, Z-axis motor 175, transmission mechanism 176, liquid receiver 178, rail 175a (see FIG. 18), pulleys 176d, belt 176e, and rail 178c.

Second support part 171b supports handling member 120 being able to move in the top-bottom direction (Z direction). Specifically, slider 175b attached to handling member 120 (see FIG. 18) engages movably with rail 175a. Handling member 120 moves in the Z direction along rail 175a as Z-axis motor 175 drives. Thus, Z-axis motor 175's drive activates belt 176e. As belt 176e drives, handling member 120 attached to belt 176e moves in the Z direction.

Second support part 171b supports tray 178a of liquid receiver 178 movable horizontally. In other words, second support part 171b supports tray 178a of liquid receiver 178 movable in a front-rear direction (Y direction). Slider 178d connected to tray 178a (see FIG. 18) engages movably with rail 178c. Tray 178a moves along rail 178c in the Y direction as Z-axis motor 175 drives. Hence, Z-axis motor 175's drive activates belt 176e. As belt 176e drives, tray 178a connected to belt 176e moves in the Z direction.

Thus, liquid receiver 178 moves horizontally linking to or together with the vertical movement of handling member 120. In other words, tray 178a of liquid receiver 178 moves horizontally linking to the downward movement of handling member 120 and leaves from the descending area of handling member 120. Tray 178a moves horizontally linking to the upward movement of handling member 120 and positions under or directly below handling member 120. Thus, when handling member 120 moves downward, tray 178a moves away from smear slide 11 held by handling member 120 not to contact. When handling member 120 moves upward, tray 178a quickly moves under or directly below smear slide 11 held by handling member 120. Consequently, it can effectively prevent liquid dropped from smear slide 11 from attaching or adhering to other parts and avoid causing troubles to move smear slide 11 at the same time.

Drivers to move tray 178a horizontally and handling member 120 vertically are the same Z-axis motor 175. This can reduce the number of parts compared to the one with separate drivers. Sharing the driver enables vertical movement of handling member 120 and horizontal movement of tray 178a to link easily.

Y-axis rail 172 is positioned extending along the Y direction. Y-axis rail 172 directs or guides Y-direction movement of first support part 171a with handling member 120 and liquid receiver 178.

Y-axis motor 174 rotates pulley 174a. Pulleys 174a and 174b locate apart in the Y direction, and belt 174c is wound around pulleys 174a and 174b. Belt 174c is also connected to second support part 171b. A mechanism to move second support part 171b in the Y direction is not necessary to be a mechanism of a motor and belt/pulley. For example, a linear motor mechanism or a ball screw mechanism can also be used to move second support part 171b in the Y direction.

Figure 18:
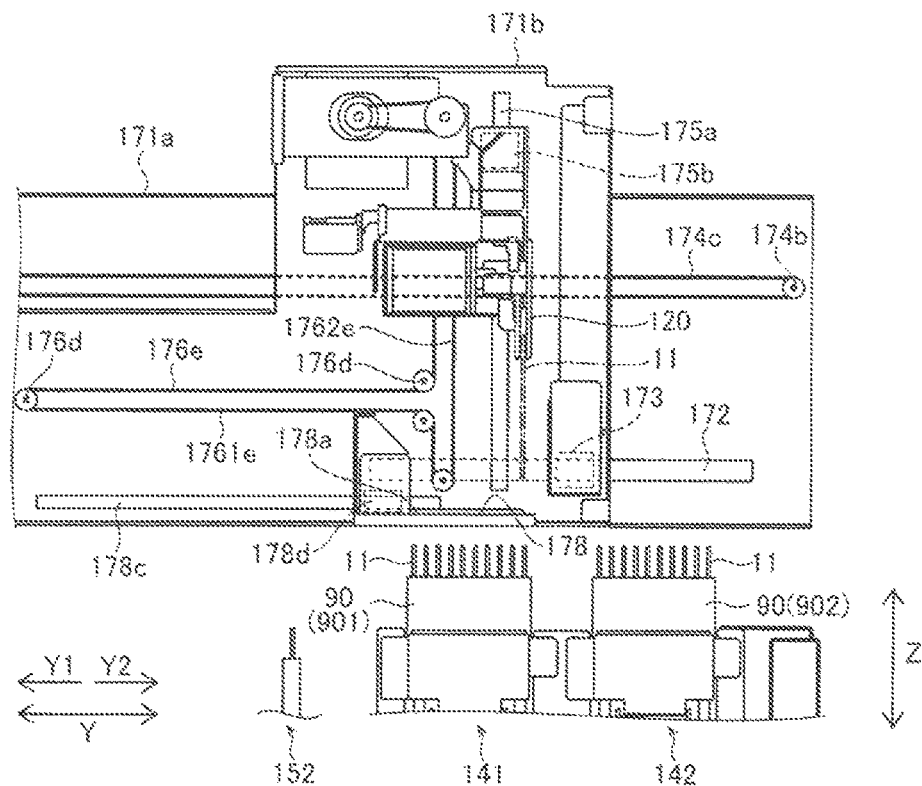
FIG. 18 is a first diagram for explaining movement of a smear transfer part in the smear transporting apparatus.

Z-axis motor 175 rotates pulley 176a. Pulleys 176a and 176b position apart in the Y direction. Belt 176c is wound around pulleys 176a and 176b. The diameter of pulley 176a is smaller than the diameter of pulley 176b, so rotation speed of Z-axis motor 175 is conveyed to pulley 176b with a reduction. In other words, pulley 176b rotates more slowly than pulley 176a rotates. Belt 176e is wound around pulley 176b and also around pulleys 176d with T-shaped. In other words, belt 176e includes a part to extend vertically connected to handling member 120 and a part to extend horizontally connected to tray 178a. As illustrated in FIG. 18, belt 176e as a link mechanism is connected to both liquid receiver 178 and handling member 120. Liquid receiver 178 connects to horizontal part 1761e, which extends horizontally, of belt 176e. Handling member 120 connects to vertical part 1762e, which extends vertically, of belt 176e.

Drive of belt 176e moves handling member 120 and tray 178a together. Specifically, as handling member 120 moves downward, tray 178a moves backward. Also, as handling member 120 moves upward, tray 178a moves forward. A mechanism to move handling member 120 in the Z direction and tray 178a in the Y direction does not have to be a motor and belt/pulley mechanism. For example, a linear motor mechanism and a ball screw mechanism may be used to move handling member 120 in the Z direction and tray 178a in the Y direction. It is not necessary to use the same belt to interlock and move handling member 120 and tray 178a. For example, a drive mechanism may be used for each handling member 120 and tray 178a and control them to move together.

[Protruding Part]

Tray 178a is possible to receive, collect or catch liquid dropped from above. Specifically, tray 178a forms a concave shape including base 178e and side 178f. The height of side 178f of tray 178a is low. The value of height of smear slide 11 is smaller than the value of width of smear slide 11. Thus, the user can easily touch base 178e and wipe off liquid collected in tray 178a. Tray 178a is formed L-shape from the X-direction view. This shape makes the length of the Y direction of tray 178a longer and the user be able to handle tray 178a easily. Also, tray 178a is made of metal, such as aluminum alloy, which enables to improve oil resistance compared to tray 178a made of resin. The top of tray 178a connects to belt 176e.

Base 178e of tray 178a contains protruding parts 178b. Protruding parts 178b sticks out from base 178e. Each protruding part 178b positions apart with a distance narrower than the thickness of smear slide 11. This distance prevents smear slide 11 from clinging to base 178e even if smear slide 11 drops on to tray 178a with any reason. If protruding part 178b does not exist, the surfaces of base 178e and smear slide 11 may contact and adhere due to liquid collected in base 178e. Thus, providing protruding part 178b makes it possible to easily remove smear slide 11 form tray 178a even if smear slide 11 drops on to tray 178a.

Rail 178c is positioned to extend in the Y direction and directs or guides slider 178d with tray 178a to move in the Y direction.

[Movements of the Smear Transfer Unit and Liquid Receiver]

Movements of smear transfer part 170 and liquid receiver 178 are explained referring to FIG. 18 to FIG. 23.

Figure 19:
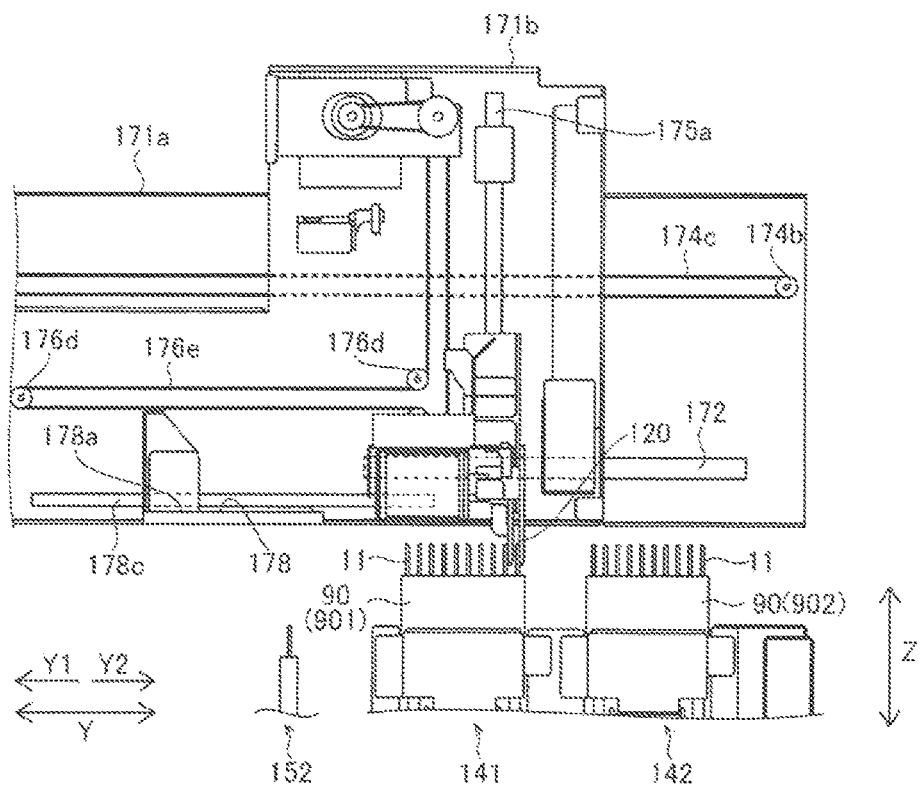
FIG. 19 is a second diagram for explaining movement of the smear transfer part in the smear transporting apparatus.

Transfer of smear slide 11 by smear transfer part 170 is explained. First, handling member 120 of smear transfer part 170, as illustrated in FIG. 18, moves to a position above first smear container 901 which accommodates smear slides 11 before smear-image capture apparatus 200 captures images of smear slides 11. Second, handling member 120 descends to a position to grip smear slide 11 accommodated in first smear container 901 and grips smear slide 11 as illustrated in FIG. 19. Then, handling member 120 ascends to a position above smear container 901 as illustrated in FIG. 18. In other words, the position of handling member 120 above first smear container 901 is a position directly above first smear container 901 or a position facilitating a lift, pick or grip of smear slide 11 from first smear container 901.

Figure 20:
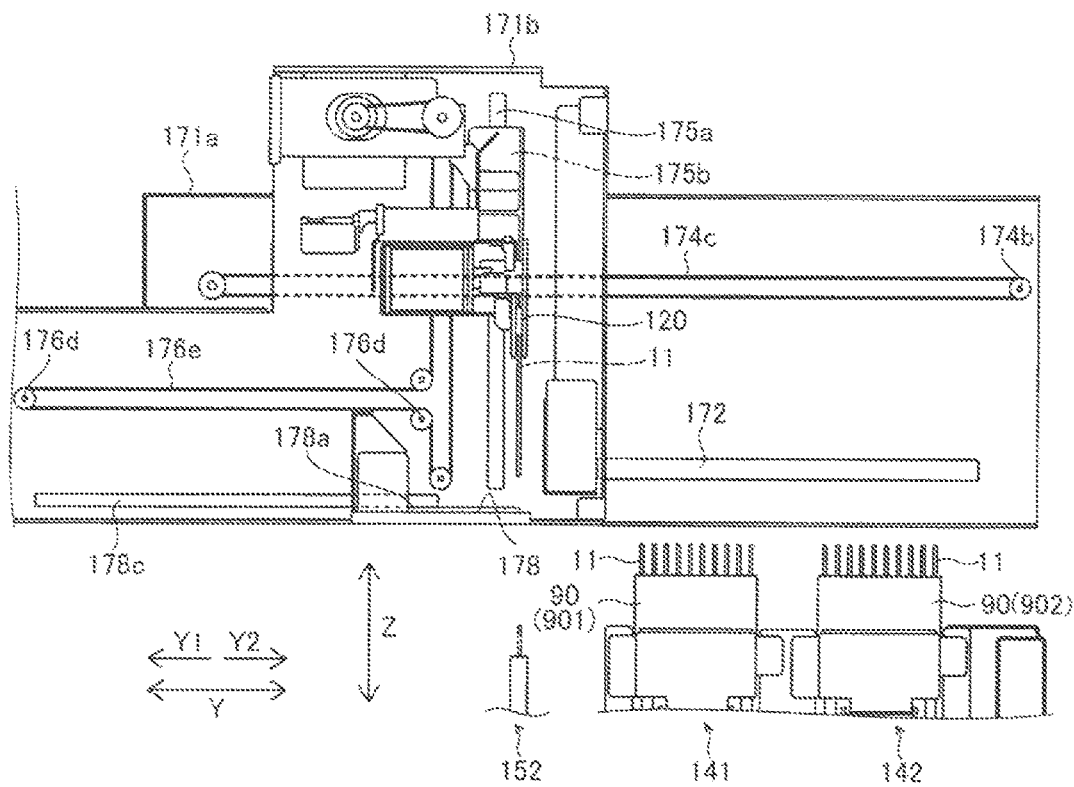
FIG. 20 is a third diagram for explaining movement of the smear transfer part in the smear transporting apparatus.
Figure 21:
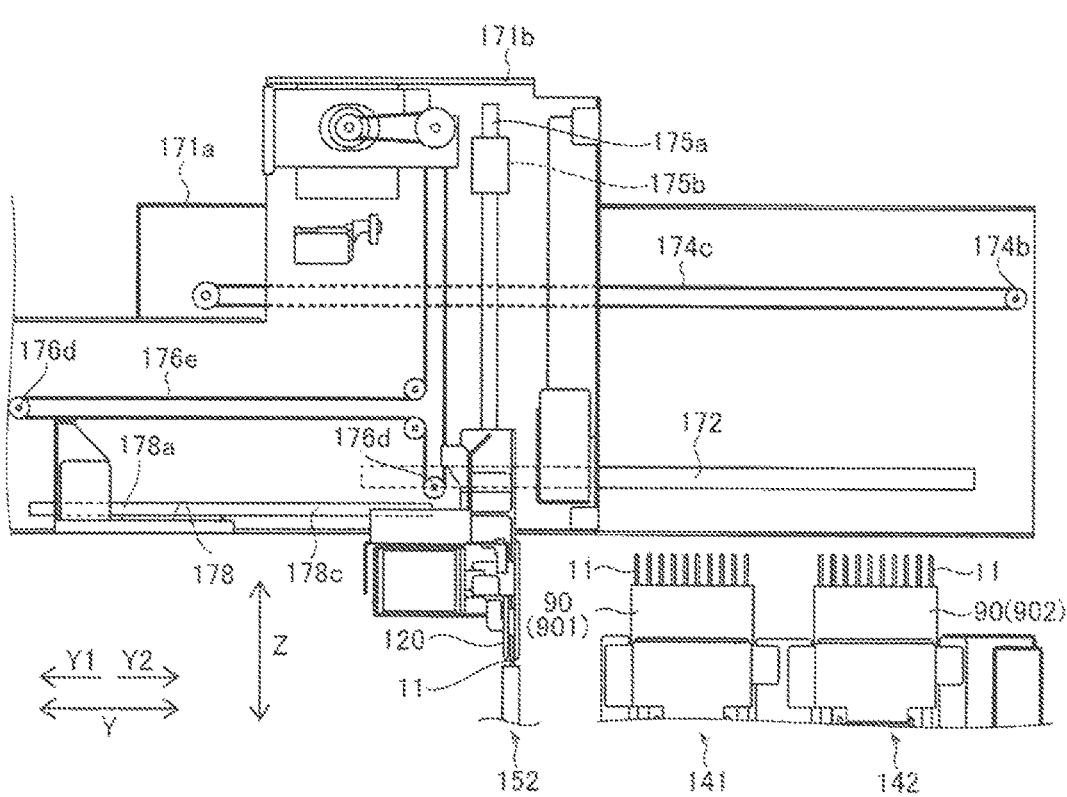
FIG. 21 is a forth diagram for explaining movement of the smear transfer part in the smear transporting apparatus.

As illustrated in FIG. 20, handling member 120 moves to above transport case 152. As FIG. 21 illustrates, handling member 120 descends toward transport case 152 and places smear slide 11 whose image is to be captured into transport case 152. Then, handling member 120 ascends, and transport case 152 transports smear slide 11 to smear-image capture apparatus 200. In other words, the position of handling member 120 above transport case 152 is a position directly above transport case 152 or a position facilitating an insertion of smear slide 11 gripped by handling member 120 into transport case 152.

After an image of smear slide 11 has been captured, transport case 152 returns smear slide 11, and handling member 120 moves above transport case 152 as illustrated in FIG. 20. Then, as FIG. 21 illustrates, handling member 120 descends and grips smear slide 11 accommodated in transport case 152. In other words, the position of handling member 120 above transport case 152 is also a position directly above transport case 152 or a position facilitating a lift, pick or grip of smear slide 11 from transport case 152.

Figure 22:
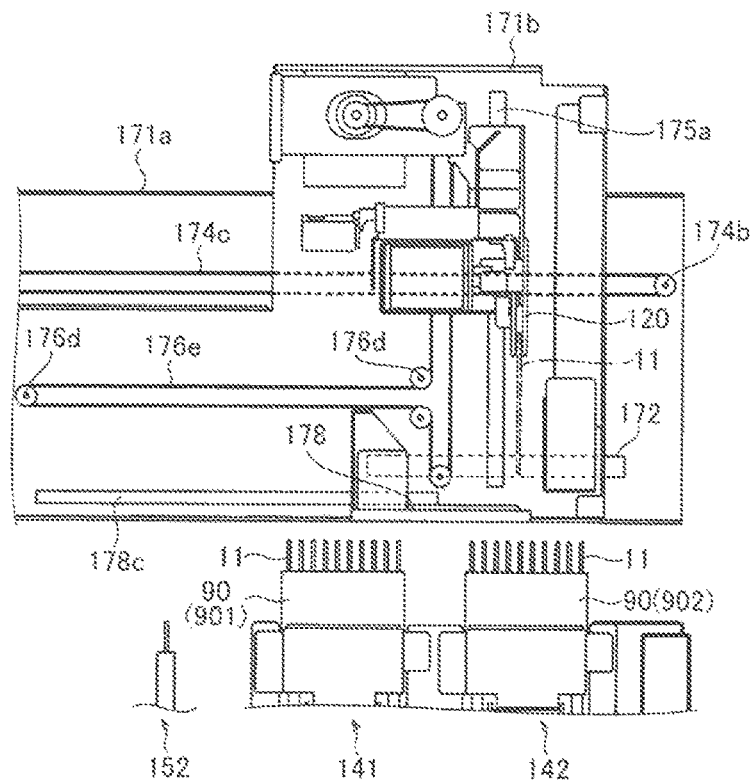
FIG. 22 is a fifth diagram for explaining movement of the smear transfer part in the smear transporting apparatus.
Figure 23:
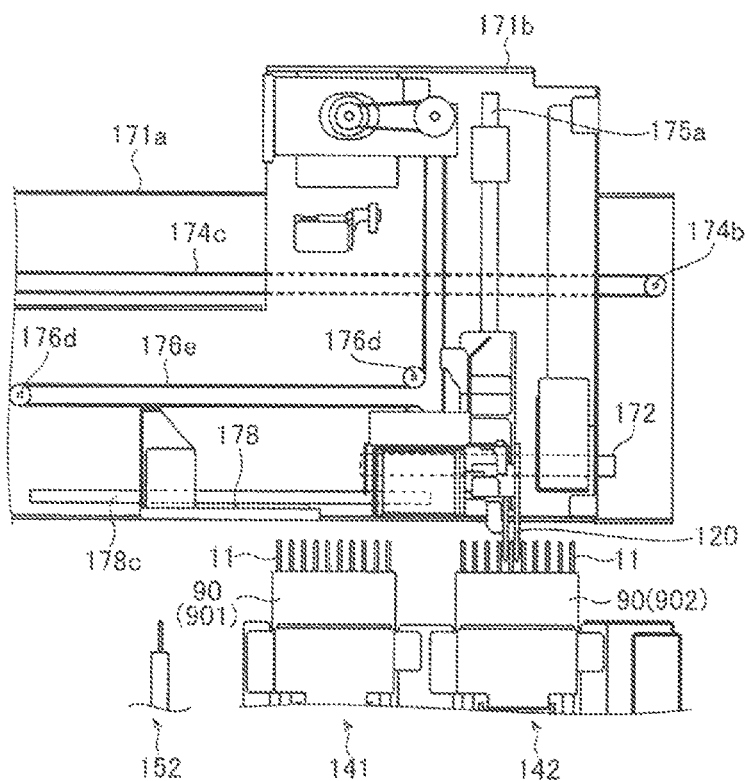
FIG. 23 is a sixth diagram for explaining movement of the smear transfer part in the smear transporting apparatus.
Figure 24:
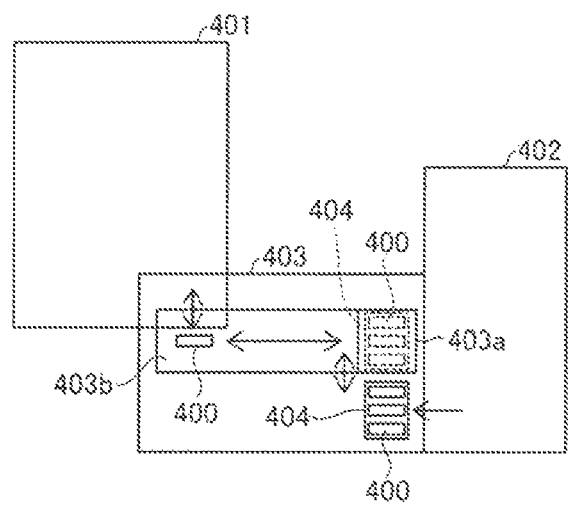
FIG. 24 is a schematic view of a conventional smear transporting apparatus.

As illustrated in FIG. 22, handling member 120 passes over first smear container 901 accommodating smear slides 11 whose images are to be captured and moves to a position above second smear container 902 accommodating smear slides 11 whose images have been captured by smear-image capture apparatus 200. Then, as FIG. 23 illustrates, handling member 120 descends toward second smear container 902, places smear slide 11 whose image has been captured in second smear container 902, and then ascends. In other words, the position of handling member 120 above second smear container 902 is a position directly above second smear container 902 or a position facilitating an insertion of smear slide 11 gripped by handling member 120 into second smear container 902.

Smear transfer part 170 is configured to transport smear slide 11 whose image has been captured to second smear container 902 passing over first smear container 901. Since this enables liquid receiver 178 to receive or collect liquid dropped from smear slide 11 when smear slide 11 passes over first smear container 901, it can effectively prevent liquid from dropping on and attaching or adhering to or into first smear container 901 which accommodates smear slides 11 whose images are to be captured.

Note that controllers 80, 110, 202, and the like may be implemented such that, for example, a circuitry such as one or more central processing units (CPUs) or processors executes a predetermined program(s).

The invention claimed is:

1. A smear transporting apparatus that transports a smear slide on which a sample is smeared to a smear-image capture apparatus, the smear transporting apparatus comprising:
   a smear-container transport part that transports a first smear container accommodating smear slides to a smear pickup position, the smear slides including a smear slide whose image is to be captured by the smear-image capture apparatus and a smear slide whose image is not to be captured by the smear-image capture apparatus;
   a smear transfer part that picks a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and
   a storage that stores the first smear container and the second smear container.

2. The smear transporting apparatus according to claim 1, wherein the smear transfer part transfers the smear slide picked up from the first smear container to the smear-image capture apparatus, while a smear slide whose image is not to be captured by the smear-image capture apparatus remains accommodated in the first smear container.

3. The smear transporting apparatus according to claim 1, wherein
   the smear-container transport part comprises:
      a first transport part that transports the first smear container accommodating the smear slides to the smear pickup position, and that transports the first smear container to the storage; and
      a second transport part that transports the second smear container accommodating the smear slide whose image has been captured by the smear-image capture apparatus to the storage.

4. The smear transporting apparatus according to claim 3, further comprising:
   a first supply region where a first smear container accommodating smear slides is received from a smear preparing apparatus that prepares a smear slide; and
   a second supply region where a second smear container accommodating no smear slide is disposed, wherein
   the first transport part transports, to the storage, the first smear container that is supplied to the first supply region and transported to the smear pickup position, and
   the second transport part transports, to the storage, the second smear container that is supplied to the second supply region and accommodates the smear slide whose image has been captured by the smear-image capture apparatus.

5. The smear transporting apparatus according to claim 4, wherein the first supply region comprises a region where a smear container accommodating a smear slide prepared manually is set.

6. The smear transporting apparatus according to claim 1, wherein the smear transfer part transfers the smear slide whose image is to be captured from the first smear container to the smear-image capture apparatus according to identification information acquired from the smear slide picked by the smear transfer part.

7. The smear transporting apparatus according to claim 6, further comprising an identification-information acquisition part that acquires the identification information provided to the smear slide, wherein the identification-information acquisition part comprises an image capture part that captures an image of a smear slide, and the smear slide is transferred to the smear-image capture apparatus in a case where the image of the smear slide captured by the image capture part includes identification information indicating that an image of the smear slide is to be captured by the smear-image capture apparatus.

8. The smear transporting apparatus according to claim 1, wherein the smear-image capture apparatus comprises an oil applier that applies an oil to the sample smeared on the smear slide.

9. A smear image capture system comprising:
a smear-image capture apparatus that captures an image of a smear slide on which a sample is smeared; and
a smear transporting apparatus that transports the smear slide to the smear-image capture apparatus, wherein
the smear transporting apparatus comprises:
 a smear-container transport part that transports a first smear container accommodating smear slides to a smear pickup position, the smear slides including a smear slide whose image is to be captured by the smear-image capture apparatus and a smear slide whose image is not to be captured by the smear-image capture apparatus;
 a smear transfer part that picks a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and
 a storage that stores the first smear container and the second smear container.

10. The smear image capture system according to claim 9, wherein the smear transfer part transfers the smear slide picked up from the first smear container to the smear-image capture apparatus, while a smear slide whose image is not to be captured by the smear-image capture apparatus remains accommodated in the first smear container.

11. A smear analysis system comprising:
a smear preparing apparatus that prepares a smear slide on which a sample is smeared;
a smear-image capture apparatus that captures an image of the smear slide on which the sample is smeared; and
a smear transporting apparatus that transports the smear slide supplied from the smear preparing apparatus to the smear-image capture apparatus, wherein
the smear transporting apparatus comprises:
 a smear-container transport part that transports a first smear container accommodating smear slides to a smear pickup position, the smear slides including a smear slide whose image is to be captured by the smear-image capture apparatus and a smear slide whose image is not to be captured by the smear-image capture apparatus;
 a smear transfer part that picks a smear slide whose image is to be captured by the smear-image capture apparatus from the first smear container transported to the smear pickup position, transfers the smear slide to the smear-image capture apparatus, and places the smear slide whose image has been captured by the smear-image capture apparatus in a second smear container different from the first smear container; and
 a storage that stores the first smear container and the second smear container.

12. The smear analysis system according to claim 11, wherein the smear transfer part transfers the smear slide picked up from the first smear container to the smear-image capture apparatus, while a smear slide whose image is not to be captured by the smear-image capture apparatus remains accommodated in the first smear container transported to the smear pickup position.

* * * * *